US012571013B2

(12) United States Patent
Xie et al.

(10) Patent No.: US 12,571,013 B2
(45) Date of Patent: Mar. 10, 2026

(54) GENE ENGINEERING BACTERIA FOR PRODUCING L-ARGININE AND CONSTRUCTION METHOD AND APPLICATION OF GENE ENGINEERING BACTERIA

(71) Applicant: Ningxia Eppen Biotech Co., LTD, Yinchuan (CN)

(72) Inventors: Xixian Xie, Tianjin (CN); Shuai Jiang, Tianjin (CN); Chenhui Wen, Tianjin (CN); Heyun Wu, Tianjin (CN); Yining Liu, Tianjin (CN); Xuan Li, Tianjin (CN); Daoguang Tian, Tianjin (CN); Bo Xiong, Tianjin (CN)

(73) Assignee: NINGXIA EPPEN BIOTECH CO., LTD, Yinchuan (CN)

( * ) Notice: Subject to any disclaimer, the term of this patent is extended or adjusted under 35 U.S.C. 154(b) by 823 days.

(21) Appl. No.: 17/781,124

(22) PCT Filed: May 15, 2020

(86) PCT No.: PCT/CN2020/090626
§ 371 (c)(1),
(2) Date: May 31, 2022

(87) PCT Pub. No.: WO2021/109467
PCT Pub. Date: Jun. 10, 2021

(65) Prior Publication Data
US 2022/0411833 A1     Dec. 29, 2022

(30) Foreign Application Priority Data

Dec. 2, 2019  (CN) .......................... 201911211097.X

(51) Int. Cl.
| | |
|---|---|
| *C12P 13/10* | (2006.01) |
| *C12N 1/20* | (2006.01) |
| *C12N 1/205* | (2026.01) |
| *C12N 9/00* | (2006.01) |
| *C12N 15/70* | (2006.01) |
| *C12R 1/19* | (2006.01) |

(52) U.S. Cl.
CPC .............. *C12P 13/10* (2013.01); *C12N 1/205* (2021.05); *C12N 9/93* (2013.01); *C12N 15/70* (2013.01); *C12Y 603/04016* (2013.01); *C12N 2800/101* (2013.01); *C12R 2001/19* (2021.05)

(58) Field of Classification Search
CPC ........... C12P 13/10; C12N 1/205; C12N 9/93; C12N 15/70; C12N 2800/101; C12N 9/1029; C12N 9/88; C12N 15/52; C12N 2310/20; C12N 9/80; C12N 15/77; C12Y 603/04016; C12Y 203/01109; C12Y 305/01016; C12Y 401/01019; C12Y 603/05005; C12R 2001/19; C12R 2001/15
See application file for complete search history.

(56) References Cited

FOREIGN PATENT DOCUMENTS

| | | | |
|---|---|---|---|
| CN | 1270223 | A | 10/2000 |
| CN | 1405302 | A | 3/2003 |
| CN | 101374940 | A | 2/2009 |
| CN | 102154160 | A | 8/2011 |
| CN | 105062941 | A | 11/2015 |
| CN | 105062943 | A | 11/2015 |
| CN | 109234220 | A | 1/2019 |
| CN | 109266675 | A | 1/2019 |
| CN | 110184230 | A | 8/2019 |
| WO | WO-2019136618 A1 * | 7/2019 | ............... C12N 1/20 |

OTHER PUBLICATIONS

Wang et al (Biotechnol Lett, Date Published: Oct. 16, 2017, https://doi.org/10.1007/s10529-017-2453-8, examiner cited) {herein Wang}. (Year: 2017).*
International Search Report issued in PCT/CN2020/090626; mailed Sep. 8, 2020; 10 pgs.
First Office Action issued in priority Chinese application No. 201911211097.X; mailed; mailed Feb. 3, 2021; 16 pgs (see English Abstract).
Xuelan, Chen et al.; Studies on the Genetic Engineering Strains Producing L-Arginine; Food and Fermentation Industries; Feb. 20, 2003; vol. 29, No. 12; pp. 97-102 (see English Abstract).
Yang, Shaomei et al.; Effect of key-gene modification on uridine biosynthesis in Bacillus subtilis; Acta Microbiologica Sinica; 2016, vol. 56, No. 1, pp. 56-67 (see English Abstract).
ChengG Gong, et al.; Progress in biosynthesis and metabolic engineering of L-Arginine producer; Microbiology China; Jun. 20, 2016, vol. 43, No. 6; pp. 1379-1387.
Xu, Meijuan, et al.; Heterologous and homologous expression of the arginine biosynthetic argC~H cluster from Corynebacterium crenatum for improvement of (L)-arginine production; J Ind Microbiol Biotechnol; 2012; vol. 39; pp. 495-502.
Park, Seok Hyun, et al.; Metabolic Engineering of Corynebacterium glutamicum for L-arginine production; Nature Communications; 2014, 5:4618; 9 pgs.
Ginesy, Mireille, et al.; Metabolic engineering of *Escherichia coli* for enhanced arginine biosynthesis; Microbial Cell Factories; 2015; vol. 14, No. 29; 11 pgs.

* cited by examiner

*Primary Examiner* — Manjunath N Rao
*Assistant Examiner* — Erica Nicole Jones-Foster
(74) *Attorney, Agent, or Firm* — HAUPTMAN HAM, LLP

(57) ABSTRACT

Disclosed are gene engineering bacteria for producing L-arginine and a construction method and an application of the gene engineering bacteria. According to the method, genes encoding a carbamoyl phosphate synthetase and a gene encoding an L-arginine biosynthesis pathway enzyme are integrated into *Escherichia coli*; the present invention has analyzed and reconstructed the arginine synthetic pathway and the metabolic flow related to arginine in the entire amino acid metabolic network in *E. coli* and finally obtained a genetically engineered bacterial strain which has a clear genetic background, carries no plasmids, undergoes no mutagenesis and is capable of stably and efficiently producing L-arginine.

6 Claims, 6 Drawing Sheets
Specification includes a Sequence Listing.

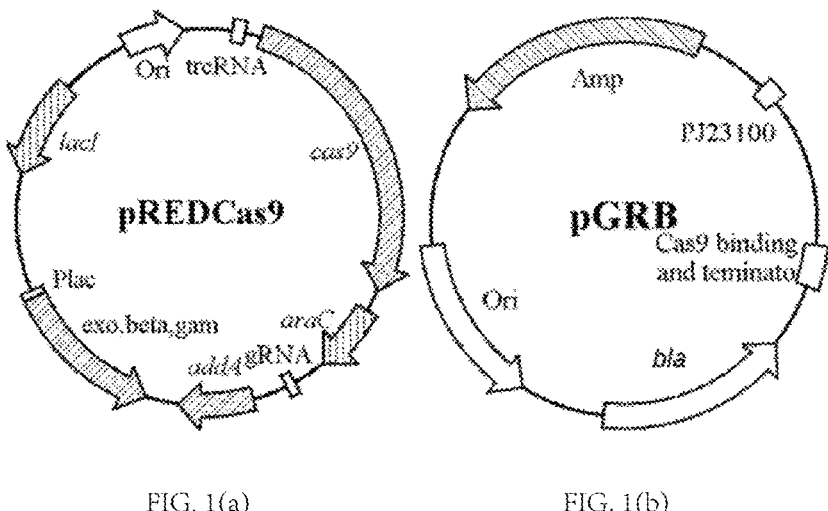
FIG. 1(a)                    FIG. 1(b)
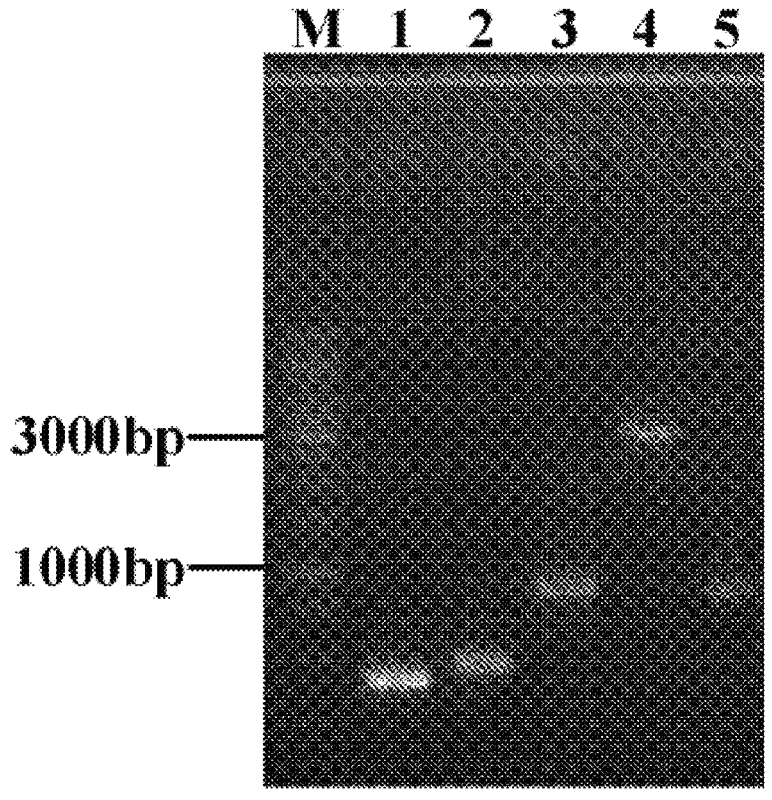
FIG. 2

SEQUENCE LISTING

<160> NUMBER OF SEQ ID NOS: 68

<210> SEQ ID NO 1
<211> LENGTH: 22
<212> TYPE: DNA
<213> ORGANISM: Artificial Sequence
<220> FEATURE:
<223> OTHER INFORMATION: Synthesized

<400> SEQUENCE: 1
ttaacctgtc tcaccgttct gg                                                  22

<210> SEQ ID NO 2
<211> LENGTH: 40
<212> TYPE: DNA
<213> ORGANISM: Artificial Sequence
<220> FEATURE:
<223> OTHER INFORMATION: Synthesized

<400> SEQUENCE: 2
acaaacctgc ctcgaactct tccgctgacg aaggcaaacc                               40

<210> SEQ ID NO 3
<211> LENGTH: 40
<212> TYPE: DNA
<213> ORGANISM: Artificial Sequence
<220> FEATURE:
<223> OTHER INFORMATION: Synthesized

<400> SEQUENCE: 3
ggtttgcctt cgtcagcgga agagttcgag gcaggtttgt                               40

<210> SEQ ID NO 4
<211> LENGTH: 21
<212> TYPE: DNA
<213> ORGANISM: Artificial Sequence
<220> FEATURE:
<223> OTHER INFORMATION: Synthesized

<400> SEQUENCE: 4
catataccag atcgccgcag t                                                   21

<210> SEQ ID NO 5
<211> LENGTH: 23
<212> TYPE: DNA
<213> ORGANISM: Artificial Sequence
<220> FEATURE:
<223> OTHER INFORMATION: Synthesized

<400> SEQUENCE: 5
cgagtttctc catcaagaca cct                                                 23

<210> SEQ ID NO 6
<211> LENGTH: 40
<212> TYPE: DNA
<213> ORGANISM: Artificial Sequence
<220> FEATURE:
<223> OTHER INFORMATION: Synthesized

<400> SEQUENCE: 6
cgcccataga gaacaggaac atgcggcttg gcaccatata                               40

<210> SEQ ID NO 7
<211> LENGTH: 40
<212> TYPE: DNA
<213> ORGANISM: Artificial Sequence

```
<220> FEATURE:
<223> OTHER INFORMATION: Synthesized

<400> SEQUENCE: 7
tatatggtgc caagccgcat gttcctgttc tctatgggcg                          40

<210> SEQ ID NO 8
<211> LENGTH: 21
<212> TYPE: DNA
<213> ORGANISM: Artificial Sequence
<220> FEATURE:
<223> OTHER INFORMATION: Synthesized

<400> SEQUENCE: 8
tatcgccgaa gttttcacca g                                             21

<210> SEQ ID NO 9
<211> LENGTH: 19
<212> TYPE: DNA
<213> ORGANISM: Artificial Sequence
<220> FEATURE:
<223> OTHER INFORMATION: Synthesized

<400> SEQUENCE: 9
ggcactcatg gcaccacct                                                19

<210> SEQ ID NO 10
<211> LENGTH: 37
<212> TYPE: DNA
<213> ORGANISM: Artificial Sequence
<220> FEATURE:
<223> OTHER INFORMATION: Synthesized

<400> SEQUENCE: 10
tgagggcatc cagttgtgcc tgcatcagcg ccgagac                            37

<210> SEQ ID NO 11
<211> LENGTH: 37
<212> TYPE: DNA
<213> ORGANISM: Artificial Sequence
<220> FEATURE:
<223> OTHER INFORMATION: Synthesized

<400> SEQUENCE: 11
gtctcggcgc tgatgcaggc acaactggat gccctca                            37

<210> SEQ ID NO 12
<211> LENGTH: 21
<212> TYPE: DNA
<213> ORGANISM: Artificial Sequence
<220> FEATURE:
<223> OTHER INFORMATION: Synthesized

<400> SEQUENCE: 12
tgaccaggga aattatacgg c                                             21

<210> SEQ ID NO 13
<211> LENGTH: 19
<212> TYPE: DNA
<213> ORGANISM: Artificial Sequence
<220> FEATURE:
<223> OTHER INFORMATION: Synthesized

<400> SEQUENCE: 13
gcccgcttca agaaactgc                                                19
```

-continued

```
<210> SEQ ID NO 14
<211> LENGTH: 76
<212> TYPE: DNA
<213> ORGANISM: Artificial Sequence
<220> FEATURE:
<223> OTHER INFORMATION: Synthesized

<400> SEQUENCE: 14
aattgttatc cgctcacaat tccacacatt atacgagccg gatgattaat tgtcaaggcg        60
cttattgaag gtgtgg        76

<210> SEQ ID NO 15
<211> LENGTH: 81
<212> TYPE: DNA
<213> ORGANISM: Artificial Sequence
<220> FEATURE:
<223> OTHER INFORMATION: Synthesized

<400> SEQUENCE: 15
tccggctcgt ataatgtgtg gaattgtgag cggataacaa tttcacacag gaaacagacc        60
atggcagaaa aaggcattac c        81

<210> SEQ ID NO 16
<211> LENGTH: 45
<212> TYPE: DNA
<213> ORGANISM: Artificial Sequence
<220> FEATURE:
<223> OTHER INFORMATION: Synthesized

<400> SEQUENCE: 16
gttgatgagc ctgattaatt gagcgccctt ttccctgctt gttag        45

<210> SEQ ID NO 17
<211> LENGTH: 45
<212> TYPE: DNA
<213> ORGANISM: Artificial Sequence
<220> FEATURE:
<223> OTHER INFORMATION: Synthesized

<400> SEQUENCE: 17
ctaacaagca gggaaaaggg cgctcaatta atcaggctca tcaac        45

<210> SEQ ID NO 18
<211> LENGTH: 22
<212> TYPE: DNA
<213> ORGANISM: Artificial Sequence
<220> FEATURE:
<223> OTHER INFORMATION: Synthesized

<400> SEQUENCE: 18
ctgtatcctt cacgtcgcat tg        22

<210> SEQ ID NO 19
<211> LENGTH: 21
<212> TYPE: DNA
<213> ORGANISM: Artificial Sequence
<220> FEATURE:
<223> OTHER INFORMATION: Synthesized

<400> SEQUENCE: 19
gcgcaacgta gaacaggaat t        21

<210> SEQ ID NO 20
<211> LENGTH: 79
```

-continued

```
<212> TYPE: DNA
<213> ORGANISM: Artificial Sequence
<220> FEATURE:
<223> OTHER INFORMATION: Synthesized

<400> SEQUENCE: 20
aattgttatc cgctcacaat tccacacatt atacgagccg gatgattaat tgtcaagatt      60
gaagcgcctt tactactcc                                                   79

<210> SEQ ID NO 21
<211> LENGTH: 85
<212> TYPE: DNA
<213> ORGANISM: Artificial Sequence
<220> FEATURE:
<223> OTHER INFORMATION: Synthesized

<400> SEQUENCE: 21
tccggctcgt ataatgtgtg gaattgtgag cggataacaa tttcacacag gaaacagacc      60
atgatcatgc ataacgtgta tggtg                                            85

<210> SEQ ID NO 22
<211> LENGTH: 86
<212> TYPE: DNA
<213> ORGANISM: Artificial Sequence
<220> FEATURE:
<223> OTHER INFORMATION: Synthesized

<400> SEQUENCE: 22
gccccaaggg gttatgctag cctacaaatt gagttatgtt catttaaata tgatgttgtt      60
cagttaagag ctgtacgcgg agttga                                           86

<210> SEQ ID NO 23
<211> LENGTH: 89
<212> TYPE: DNA
<213> ORGANISM: Artificial Sequence
<220> FEATURE:
<223> OTHER INFORMATION: Synthesized

<400> SEQUENCE: 23
ctgaacaaca tcatatttaa atgaacataa ctcaatttgt aggctagcat aaccccttgg      60
ggcgtcatag taatccagca actcttgtg                                        89

<210> SEQ ID NO 24
<211> LENGTH: 22
<212> TYPE: DNA
<213> ORGANISM: Artificial Sequence
<220> FEATURE:
<223> OTHER INFORMATION: Synthesized

<400> SEQUENCE: 24
gagcaggtat ttacgtgaac cg                                               22

<210> SEQ ID NO 25
<211> LENGTH: 23
<212> TYPE: DNA
<213> ORGANISM: Artificial Sequence
<220> FEATURE:
<223> OTHER INFORMATION: Synthesized

<400> SEQUENCE: 25
gtacgcagct tgttctgata tcg                                              23

<210> SEQ ID NO 26
```

```
<211> LENGTH: 81
<212> TYPE: DNA
<213> ORGANISM: Artificial Sequence
<220> FEATURE:
<223> OTHER INFORMATION: Synthesized

<400> SEQUENCE: 26
agttgctgga ttactatgac cctagaagaa atcaaccagc gcatcagaaa gtctcctgtg        60
catttacctc ggctggttgg c                                                  81

<210> SEQ ID NO 27
<211> LENGTH: 89
<212> TYPE: DNA
<213> ORGANISM: Artificial Sequence
<220> FEATURE:
<223> OTHER INFORMATION: Synthesized

<400> SEQUENCE: 27
atgcacagga gactttctga tgcgctggtt gatttcttct agggtcatag taatccagca        60
actgtcatag taatccagca actcttgtg                                          89

<210> SEQ ID NO 28
<211> LENGTH: 22
<212> TYPE: DNA
<213> ORGANISM: Artificial Sequence
<220> FEATURE:
<223> OTHER INFORMATION: Synthesized

<400> SEQUENCE: 28
gatatttcca tcatcgctcc tg                                                 22

<210> SEQ ID NO 29
<211> LENGTH: 40
<212> TYPE: DNA
<213> ORGANISM: Artificial Sequence
<220> FEATURE:
<223> OTHER INFORMATION: Synthesized

<400> SEQUENCE: 29
ctcgggttat accttacctg ccttacctcg gctggttggc                              40

<210> SEQ ID NO 30
<211> LENGTH: 40
<212> TYPE: DNA
<213> ORGANISM: Artificial Sequence
<220> FEATURE:
<223> OTHER INFORMATION: Synthesized

<400> SEQUENCE: 30
gccaaccagc cgaggtaagg caggtaaggt ataacccgag                              40

<210> SEQ ID NO 31
<211> LENGTH: 81
<212> TYPE: DNA
<213> ORGANISM: Artificial Sequence
<220> FEATURE:
<223> OTHER INFORMATION: Synthesized

<400> SEQUENCE: 31
caccgacaaa caacagataa aacgaaaggc ccagtctttc gactgagcct ttcgttttat        60
ttgttatcga cgtacccccg c                                                  81

<210> SEQ ID NO 32
<211> LENGTH: 89
```

-continued

```
<212> TYPE: DNA
<213> ORGANISM: Artificial Sequence
<220> FEATURE:
<223> OTHER INFORMATION: Synthesized

<400> SEQUENCE: 32
aaagactggg cctttcgttt tatctgttgt ttgtcggtga acgctctcct gagtaggaca      60
aatgtcatag taatccagca actcttgtg                                       89

<210> SEQ ID NO 33
<211> LENGTH: 21
<212> TYPE: DNA
<213> ORGANISM: Artificial Sequence
<220> FEATURE:
<223> OTHER INFORMATION: Synthesized

<400> SEQUENCE: 33
aatagttgtt gccgcctgag t                                               21

<210> SEQ ID NO 34
<211> LENGTH: 76
<212> TYPE: DNA
<213> ORGANISM: Artificial Sequence
<220> FEATURE:
<223> OTHER INFORMATION: Synthesized

<400> SEQUENCE: 34
aattgttatc cgctcacaat tccacacatt atacgagccg gatgattaat tgtcaaaaaa      60
caggcagcaa agtccc                                                     76

<210> SEQ ID NO 35
<211> LENGTH: 87
<212> TYPE: DNA
<213> ORGANISM: Artificial Sequence
<220> FEATURE:
<223> OTHER INFORMATION: Synthesized

<400> SEQUENCE: 35
tccggctcgt ataatgtgtg gaattgtgag cggataacaa tttcacacag gaaacagacc      60
atgaagagac gattagtact ggaaaac                                         87

<210> SEQ ID NO 36
<211> LENGTH: 86
<212> TYPE: DNA
<213> ORGANISM: Artificial Sequence
<220> FEATURE:
<223> OTHER INFORMATION: Synthesized

<400> SEQUENCE: 36
gccccaaggg gttatgctag cctacaaatt gagttatgtt catttaaata tgatgttgtt      60
cagagaagac atcgatagcg gaaaat                                          86

<210> SEQ ID NO 37
<211> LENGTH: 86
<212> TYPE: DNA
<213> ORGANISM: Artificial Sequence
<220> FEATURE:
<223> OTHER INFORMATION: Synthesized

<400> SEQUENCE: 37
ctgaacaaca tcatatttaa atgaacataa ctcaatttgt aggctagcat aaccccttgg      60
ggcaagcact acctgtgaag ggatgt                                          86
```

-continued

```
<210> SEQ ID NO 38
<211> LENGTH: 21
<212> TYPE: DNA
<213> ORGANISM: Artificial Sequence
<220> FEATURE:
<223> OTHER INFORMATION: Synthesized

<400> SEQUENCE: 38
cagggcttcc acagtcacaa t                                            21

<210> SEQ ID NO 39
<211> LENGTH: 21
<212> TYPE: DNA
<213> ORGANISM: Artificial Sequence
<220> FEATURE:
<223> OTHER INFORMATION: Synthesized

<400> SEQUENCE: 39
acccggtgac aggaaaaaca t                                            21

<210> SEQ ID NO 40
<211> LENGTH: 85
<212> TYPE: DNA
<213> ORGANISM: Artificial Sequence
<220> FEATURE:
<223> OTHER INFORMATION: Synthesized

<400> SEQUENCE: 40
caccgacaaa caacagataa aacgaaaggc ccagtctttc gactgagcct ttcgttttat   60
ttgtcatata gtgactgccg cctcc                                        85

<210> SEQ ID NO 41
<211> LENGTH: 86
<212> TYPE: DNA
<213> ORGANISM: Artificial Sequence
<220> FEATURE:
<223> OTHER INFORMATION: Synthesized

<400> SEQUENCE: 41
aaagactggg cctttcgttt tatctgttgt ttgtcggtga cgctctcct gagtaggaca    60 aataagcact acctgtgaag ggatgt                                       86

<210> SEQ ID NO 42
<211> LENGTH: 23
<212> TYPE: DNA
<213> ORGANISM: Artificial Sequence
<220> FEATURE:
<223> OTHER INFORMATION: Synthesized

<400> SEQUENCE: 42
accgaggagc agacaatgaa taa                                          23

<210> SEQ ID NO 43
<211> LENGTH: 76
<212> TYPE: DNA
<213> ORGANISM: Artificial Sequence
<220> FEATURE:
<223> OTHER INFORMATION: Synthesized

<400> SEQUENCE: 43
aattgttatc cgctcacaat tccacacatt atacgagccg gatgattaat tgtcaaggtg   60
atggcaacaa caggga                                                  76
```

-continued

```
<210> SEQ ID NO 44
<211> LENGTH: 82
<212> TYPE: DNA
<213> ORGANISM: Artificial Sequence
<220> FEATURE:
<223> OTHER INFORMATION: Synthesized

<400> SEQUENCE: 44
tccggctcgt ataatgtgtg gaattgtgag cggataacaa tttcacacag gaaacagacc      60
atggaaattt tcgttacggg tc                                              82

<210> SEQ ID NO 45
<211> LENGTH: 87
<212> TYPE: DNA
<213> ORGANISM: Artificial Sequence
<220> FEATURE:
<223> OTHER INFORMATION: Synthesized

<400> SEQUENCE: 45
caccgacaaa caacagataa aacgaaaggc ccagtctttc gactgagcct ttcgttttat      60
ttgttagccc atcagaatca gtttcac                                         87

<210> SEQ ID NO 46
<211> LENGTH: 84
<212> TYPE: DNA
<213> ORGANISM: Artificial Sequence
<220> FEATURE:
<223> OTHER INFORMATION: Synthesized

<400> SEQUENCE: 46
aaagactggg cctttcgttt tatctgttgt ttgtcggtga acgctctcct gagtaggaca      60
aatctatcta cgcgccgttg ttgt                                            84

<210> SEQ ID NO 47
<211> LENGTH: 20
<212> TYPE: DNA
<213> ORGANISM: Artificial Sequence
<220> FEATURE:
<223> OTHER INFORMATION: Synthesized

<400> SEQUENCE: 47
gcgctggcta acatgaggaa                                                 20

<210> SEQ ID NO 48
<211> LENGTH: 56
<212> TYPE: DNA
<213> ORGANISM: Artificial Sequence
<220> FEATURE:
<223> OTHER INFORMATION: Synthesized

<400> SEQUENCE: 48
agtcctaggt ataatactag ttgcgtactt acaatattgc cgttttagag ctagaa         56

<210> SEQ ID NO 49
<211> LENGTH: 56
<212> TYPE: DNA
<213> ORGANISM: Artificial Sequence
<220> FEATURE:
<223> OTHER INFORMATION: Synthesized

<400> SEQUENCE: 49
ttctagctct aaaacggcaa tattgtaagt acgcaactag tattatacct aggact         56

<210> SEQ ID NO 50
```

-continued

```
<211> LENGTH: 56
<212> TYPE: DNA
<213> ORGANISM: Artificial Sequence
<220> FEATURE:
<223> OTHER INFORMATION: Synthesized

<400> SEQUENCE: 50
agtcctaggt ataatactag ttatcgggcc aatctatccg cgttttagag ctagaa          56

<210> SEQ ID NO 51
<211> LENGTH: 56
<212> TYPE: DNA
<213> ORGANISM: Artificial Sequence
<220> FEATURE:
<223> OTHER INFORMATION: Synthesized

<400> SEQUENCE: 51
ttctagctct aaaacgcgga tagattggcc cgataactag tattatacct aggact          56

<210> SEQ ID NO 52
<211> LENGTH: 56
<212> TYPE: DNA
<213> ORGANISM: Artificial Sequence
<220> FEATURE:
<223> OTHER INFORMATION: Synthesized

<400> SEQUENCE: 52
agtcctaggt ataatactag ttctctgcgg caccgggcaa agttttagag ctagaa          56

<210> SEQ ID NO 53
<211> LENGTH: 56
<212> TYPE: DNA
<213> ORGANISM: Artificial Sequence
<220> FEATURE:
<223> OTHER INFORMATION: Synthesized

<400> SEQUENCE: 53
ttctagctct aaaactttgc ccggtgccgc agagaactag tattatacct aggact          56

<210> SEQ ID NO 54
<211> LENGTH: 56
<212> TYPE: DNA
<213> ORGANISM: Artificial Sequence
<220> FEATURE:
<223> OTHER INFORMATION: Synthesized

<400> SEQUENCE: 54
agtcctaggt ataatactag ttgcagattt aatcactctg cgttttagag ctagaa          56

<210> SEQ ID NO 55
<211> LENGTH: 56
<212> TYPE: DNA
<213> ORGANISM: Artificial Sequence
<220> FEATURE:
<223> OTHER INFORMATION: Synthesized

<400> SEQUENCE: 55
ttctagctct aaaacgcaga gtgattaaat ctgcaactag tattatacct aggact          56

<210> SEQ ID NO 56
<211> LENGTH: 56
<212> TYPE: DNA
<213> ORGANISM: Artificial Sequence
<220> FEATURE:
<223> OTHER INFORMATION: Synthesized

<400> SEQUENCE: 56
```

-continued agtcctaggt ataatactag tggtgcctga cgaccataaa agttttagag ctagaa          56

<210> SEQ ID NO 57
<211> LENGTH: 56
<212> TYPE: DNA
<213> ORGANISM: Artificial Sequence
<220> FEATURE:
<223> OTHER INFORMATION: Synthesized

<400> SEQUENCE: 57
ttctagctct aaaactttta tggtcgtcag gcaccactag tattatacct aggact          56

<210> SEQ ID NO 58
<211> LENGTH: 63
<212> TYPE: DNA
<213> ORGANISM: Artificial Sequence
<220> FEATURE:
<223> OTHER INFORMATION: Synthesized

<400> SEQUENCE: 58
ctgaacaaca tcatatttaa atgaacataa ctcaatttgt aggctagcat aacccctttgg          60 ggc                                                                     63

<210> SEQ ID NO 59
<211> LENGTH: 86
<212> TYPE: DNA
<213> ORGANISM: Artificial Sequence
<220> FEATURE:
<223> OTHER INFORMATION: Synthesized

<400> SEQUENCE: 59
gccccaaggg gttatgctag cctacaaatt gagttatgtt catttaaata tgatgttgtt          60
cagttaagag ctgtacgcgg agttga                                             86

<210> SEQ ID NO 60
<211> LENGTH: 63
<212> TYPE: DNA
<213> ORGANISM: Artificial Sequence
<220> FEATURE:
<223> OTHER INFORMATION: Synthesized

<400> SEQUENCE: 60
atgcacagga gactttctga tgcgctggtt gatttcttct agggtcatag taatccagca          60
act                                                                     63

<210> SEQ ID NO 61
<211> LENGTH: 63
<212> TYPE: DNA
<213> ORGANISM: Artificial Sequence
<220> FEATURE:
<223> OTHER INFORMATION: Synthesized

<400> SEQUENCE: 61
agttgctgga ttactatgac cctagaagaa atcaaccagc gcatcagaaa gtctcctgtg          60
cat                                                                     63

<210> SEQ ID NO 62
<211> LENGTH: 56
<212> TYPE: DNA
<213> ORGANISM: Artificial Sequence
<220> FEATURE:
<223> OTHER INFORMATION: Synthesized -continued

<400> SEQUENCE: 62
agtcctaggt ataatactag tagggattat gaacggcaat ggttttagag ctagaa          56

<210> SEQ ID NO 63
<211> LENGTH: 56
<212> TYPE: DNA
<213> ORGANISM: Artificial Sequence
<220> FEATURE:
<223> OTHER INFORMATION: Synthesized

<400> SEQUENCE: 63
ttctagctct aaaaccattg ccgttcataa tccctactag tattatacct aggact          56

<210> SEQ ID NO 64
<211> LENGTH: 63
<212> TYPE: DNA
<213> ORGANISM: Artificial Sequence
<220> FEATURE:
<223> OTHER INFORMATION: Synthesized

<400> SEQUENCE: 64
ctgaacaaca tcatatttaa atgaacataa ctcaatttgt aggctagcat aaccccttgg          60
ggc          63

<210> SEQ ID NO 65
<211> LENGTH: 63
<212> TYPE: DNA
<213> ORGANISM: Artificial Sequence
<220> FEATURE:
<223> OTHER INFORMATION: Synthesized

<400> SEQUENCE: 65
gccccaaggg gttatgctag cctacaaatt gagttatgtt catttaaata tgatgttgtt          60
cag          63

<210> SEQ ID NO 66
<211> LENGTH: 56
<212> TYPE: DNA
<213> ORGANISM: Artificial Sequence
<220> FEATURE:
<223> OTHER INFORMATION: Synthesized

<400> SEQUENCE: 66
agtcctaggt ataatactag tggaagagtt gccgcgcatc agttttagag ctagaa          56

<210> SEQ ID NO 67
<211> LENGTH: 56
<212> TYPE: DNA
<213> ORGANISM: Artificial Sequence
<220> FEATURE:
<223> OTHER INFORMATION: Synthesized

<400> SEQUENCE: 67
ttctagctct aaaactgatg cgcggcaact cttccactag tattatacct aggact          56

<210> SEQ ID NO 68
<211> LENGTH: 687
<212> TYPE: DNA
<213> ORGANISM: Artificial Sequence
<220> FEATURE:
<223> OTHER INFORMATION: Synthesized

<400> SEQUENCE: 68
atggaaattt tcgttacggg tctgctgctg ggtgccagtc tgctgctggc catcggtccg          60

-continued

```
cagaacgtgc tcgtgatcaa acaaggcatc aagcgcgaag gtatcaccgc ggttatcatc    120
gtgtgtctgc tgagcgacgt tgtgctgttc acgctgggca cgctgggcgt tggtctgatc    180
agcgataccg cgccgatcat tctggatatt ctgcgctggt gcggtatcgc ctatctgctg    240
tggtttgcgg ttatggccgc gcgtgatgcg ctgcgtgcgc gtaccgaagt gacgttcgtt    300
gaacacagcg aaccagttgc cgcggccagt gcgagtggtg gtggtgttac gaccaaacag    360
cgcccacgtc tgcgtatcac gagcggtacc cgccaagttt gggttcgccc gatgctgatg    420
gcgatcgttc tgacgtggct gaatccgaac gcgtatctgg atgcgttcgt tttcatcggc    480
ggtgttggcg cgcagtatgg cgaaaccggt cgctggattt ttgcggcggg tgcgtttgcc    540
gcgagtctgg tttggtttcc gctggttggt tatggtgccg ccgcgctgag tcgtccactg    600
agtagcccac gcgtgtggcg ctggatcaat atcggcgttg ccgtggttct gaccggtctg    660
gcggtgaaac tgattctgat gggctaa                                        687
```

GENE ENGINEERING BACTERIA FOR PRODUCING L-ARGININE AND CONSTRUCTION METHOD AND APPLICATION OF GENE ENGINEERING BACTERIA

This application is a U.S. National Phase of International Application Number PCT/CN2020/090626, filed May 15, 2020, and claims priority from patent application No. 201911211097.X, filed with the China National Intellectual Property Administration on Dec. 2, 2019, and titled "GENE ENGINEERING BACTERIA FOR PRODUCING L-AR-GININE AND CONSTRUCTION METHOD AND APPLI-CATION OF GENE ENGINEERING BACTERIA", the disclosure of which is hereby incorporated by reference herein in its entirety.

INCORPORATION BY REFERENCE

The sequence listing provided in the file entitled Amend-ed_SQL.txt, which is an ASCII text file that was created on May 26, 2022, and which comprises 15,612 bytes, is hereby incorporated by reference in its entirety.

TECHNICAL FIELD

The present invention belongs to the technical field of gene engineering, and relates to a gene engineering bacterium capable of stably and efficiently producing L-arginine, and a construction method and an application thereof.

BACKGROUND OF THE INVENTION

L-arginine is a semi-essential basic amino acid or conditionally essential amino acid in humans and animals, and has important biochemical and physiological functions. At present, L-arginine has been widely used in medicine, industry, food, cosmetics, animal husbandry and other fields, and has important economic and social values.

The production methods of L-arginine mainly include protein hydrolysis method and microbial fermentation method. Compared with protein hydrolysis extraction method, microbial fermentation method has the advantages of relatively simple production process, relatively small environmental impact and high product purity, and is suitable for large-scale industrial production.

At present, arginine-producing strains are mainly *Corynebacterium glutamicum*, which has the problems of long fermentation period (90 h-120 h) and low production intensity in the production process. At the same time, the existing fermentation process of *Corynebacterium glutamicum* is greatly affected by the quality of excipients such as corn steep liquor, and the production is easy to fluctuate. In addition, the gene editing of *Corynebacterium glutamicum* is difficult, resulting in the use of plasmid expression vectors in the existing arginine-producing strains to strengthen the key genes related to arginine synthesis. However, in the fermentation process, the multiple copies of plasmids cause a level of burden to the growth of bacteria, resulting in a decrease in the yield in the late fermentation. Besides, during the production process, the plasmid expression vector is easily lost or a certain selective pressure needs to be added, resulting in the problem of high cost in the industrial production process. Many factors make it difficult to put the current arginine-producing strains into industrial production.

Since there are many feedback regulations in the arginine synthetic and metabolic pathways and many arginine metabolic pathways and the metabolic network involved in the precursors required for arginine synthesis is complex, the initial research and development of arginine-producing industrial strains mainly adopts a traditional mutagenesis method combined with screening of resistance to an arginine structural analogue. The selected starting strains are mainly *Brevibacterium flavum, Corynebacterium crenatum* and *Corynebacterium glutamicum*. The research strategy focuses on screening mutants of arginine structural analogues to relieve the feedback regulations in the process of arginine synthesis and improve the intracellular accumulation of L-arginine. Among them, Li Shaoping, et al. screened a *Corynebacterium crenatum* strain with histidine deficiency, sulfaguanidine resistance, D-arginine resistance, homoarginine resistance and S-methylcysteine resistance by NTG stepwise mutagenesis (CN201010610917.5), and after the fermentation experiment, the L-arginine accumulation was 32.8 g/L when it was cultured in a 5 L fermenter for 96 h. However, the L-arginine-producing strain obtained through mutagenesis and screening using a structural analogue is difficult to put into large-scale industrial production due to its poor genetic stability and easy to produce back mutations and other shortcomings.

With the rapid development of gene engineering technology, the construction method of L-arginine-producing strains using metabolic engineering technology has gradually replaced traditional mutagenesis breeding methods. In *Corynebacterium glutamicum*, there are no genes involved in the degradation of arginine; and the metabolic flux of intracellular glucose uptaken by *Corynebacterium glutamicum* going through the glycolysis pathway to produce glutamic acid, one of the main precursors of arginine synthesis, is strong, so *Corynebacterium glutamicum* is the main choice for constructing L-arginine-producing strains. Xu Meijuan et al. (Xu M, Rao Z, Yang J, et al. J Ind Microbiol Biotechnol, 2012, 39 (3): 495-502.) The gene cluster argCJBDERGH for synthesizing L-arginine was ligated into the pJCtac shuttle expression vector and introduced into *Corynebacterium crenatum*. After 96 h fermentation, the yield of L-arginine of the strain was increased to 45.6 g/L. Park et al. (Park S H, Kim H U, Kim T Y, et al. Nature Communications, 2014, 5:4618) used *Corynebacterium glutamicum* as the starting strain to increase the tolerance of glutamine to L-arginine structural analogues by random mutagenesis, and systematic metabolic engineering technology to relieve feedback inhibition in the process of arginine synthesis, strengthen the supply of NADPH during the synthesis process, and enhance the supply of precursors. Finally, after 96 h fermentation in a 5 L fermenter, the accumulation of L-arginine was 92.5 g/L, the conversion rate was 0.35 g arginine/g glucose, and the maximum production intensity was 0.9 g arginine/L/h. The above-mentioned L-arginine producing strains generally have the problems of long production cycle and low production intensity. In addition, in the process of strain construction, the key genes of arginine synthesis are ligated into the expression vector to increase the transcription amounts of key enzymes, thereby enhancing the metabolic flux of the arginine synthetic pathway. However, in the production process, the expression vector is easily lost or a certain selective pressure needs to be added, so it is difficult to put the strains into industrial production.

Due to the advantages of short fermentation period, clear genetic background, convenient molecular manipulation and stable fermentation process, *Escherichia coli* has become a better choice for the construction of L-arginine-producing industrial strains. Ginesy et al. (Ginesy M, Belotserkovsky J, Enman J, et al. Microbial Cell Factories, 2015, 14 (1): 29.) used *Escherichia coli* as the starting strain, knocked out the argR gene to relieve the feedback repression of arginine, integrated the mutant gene argA214 (H15Y) to relieve the feedback repression of arginine to ArgA, knocked out the arginine degradation related gene adiA, and knocked out the ornithine degradation related genes speC and speF, so that more carbon flux of intermediate metabolites flowed to L-arginine. After 42 h culture in a 1 L fermenter, the accumulation of L-arginine reached 11.64 g/L, the conversion rate was 0.44 g arginine/g glucose, and the production intensity was 0.29 g arginine/L/h. Although the fermentation period of this strain is obviously shortened, its arginine accumulation and production intensity have not yet met the requirements of industrial production.

SUMMARY OF THE INVENTION

In view of the above-mentioned problems, the purpose of the present invention is to provide a gene engineering bacterium capable of stably and efficiently producing L-arginine, and a construction method and an application thereof. The engineering bacterium has good industrial application prospects.

The present invention provides the following technical solutions:

In a first aspect, the present invention provides a genetically engineered bacterial strain for producing L-arginine, which contains the genes encoding a carbamoyl phosphate synthetase, pyrAA and pyrAB.

In one embodiment, the genetically engineered bacterial strain takes *Escherichia coli* or *Corynebacterium glutamicum* as the starting strain, such as *E. coli* W3110 or *E. coli* MG1655.

In one embodiment, the pyrAA and pyrAB genes are integrated into the yjiT gene locus of *E. coli*.

In one embodiment, the pyrAA and pyrAB genes are derived from *Bacillus subtilis*, in particular, the pyrAA and pyrAB genes are derived from the genes encoding a carbamoyl phosphate synthetase in *B. subtilis* A260.

In one embodiment, the genetically engineered bacterial strain further contains a gene encoding a L-arginine biosynthesis pathway enzyme selected from one or more of the following enzymes: argC, argJ, argB, argD, argF, argG, argH; the gene encoding the L-arginine biosynthesis pathway enzyme is derived from *Corynebacterium glutamicum* ATCC13032; in one embodiment, the gene encoding the L-arginine biosynthesis pathway enzyme is promoted by a Pire promoter; in one embodiment, the gene encoding the L-arginine biosynthesis pathway enzyme is integrated into the yghX gene locus of *E. coli*.

In one embodiment, the genetically engineered bacterial strain further contains a gene lysE encoding an arginine transporter (NCBI Reference Sequence: WP_143758438.1), and the transporter gene is derived from *Corynebacterium efficiens*; in one embodiment, the lysE gene is integrated into the ilvG gene locus of *E. coli*.

In one embodiment, the genetically engineered bacterial strain does not contain a gene degrading L-arginine, which can be obtained by knocking out one or more of the following genes: a gene encoding an arginine decarboxylase, a gene encoding an arginine succinyltransferase, a gene encoding an acetylornithine deacetylase. The gene encoding an arginine decarboxylase includes at least one of speA (NCBI-GeneID: 12933352) and adiA (NCBI-GeneID: 12934085); the gene encoding an arginine succinyltransferase is astA (NCBI-GeneID: 12933241); the gene encoding an acetylornithine deacetylase is argli (NCBI-GeneID: 12930574). In one embodiment, the genetically engineered bacterial strain is *E. coli* with the speA, adiA and astA genes simultaneously knocked out.

In one embodiment, the genetically engineered bacterial strain contains the pyrAA, pyrAB, argC, argJ, argB, argD, argF, argG, argH and lysE genes. In one embodiment, the genetically engineered bacterial strain does not contain the speA, adiA, astA and argli genes.

In the present invention, the pyrAA, pyrAB, argC, argJ, argB, argD, argF, argG, argH, lysE, speA, adiA, astA and argli genes are not limited to wild-type genes, but can also be mutants encoding corresponding proteins or artificially modified genes, the corresponding proteins including substitution, deletion or addition of one or more amino acid residues at one or more sites, as long as the proteins encoded by the mutants or the artificially modified genes have the corresponding activities and have no functional defects. These genes have been registered in GenBank, and those skilled in the art can obtain these genes by PCR. As an example, the pyrAA gene is NCBI-GeneID: 937368, the pyrAB gene is NCBI-GeneID: 936608, the arg (gene is NCBI-GeneID: 1019370, the argJ gene is NCBI-GeneID: 1019371, the argB gene is NCBI-GeneID: 1019372, the argD gene is NCBI-GeneID: 1019373, the argF gene is NCBI-GeneID: 1019374, the argG gene is NCBI-GeneID: 1019376, the argH gene is NCBI-GeneID: 1019377, the lysE gene has the nucleotide sequence shown in SEQ ID NO: 68 (NCBI Sequence ID: WP_143758438.1), the speA gene is NCBI-GeneID: 12933352, the adiA gene is NCBI-GeneID: 12934085, the astA gene is NCBI-GeneID: 12933241 and the argli gene is NCBI-GeneID: 12930574.

In a second aspect, the present invention provides a construction method of the above-mentioned genetically engineered bacterial strain, comprising the following step: (1) integrating pyrAA and pyrAB genes into the genome of a starting strain.

For example, the starting strain is *E. coli*, such as, *E. coli* W3110 (ATCC27325).

In one embodiment, the construction method further optionally comprises one or more of the following steps:

(2) integrating arginine biosynthesis pathway enzyme genes, including one or more of argC, argJ, argB, argD, argF, argG, argH genes; and/or integrating a lysE gene encoding an arginine transporter;

(3) knocking out of a gene encoding an arginine decarboxylase, a gene encoding an arginine succinyltransferase, and/or a gene encoding an acetylornithine deacetylase; for example, the gene encoding an arginine decarboxylase includes at least one of speA and adiA genes; the gene encoding an arginine succinyltransferase is astA gene; the gene encoding an acetylornithine deacetylase is argE gene.

In one embodiment, the construction method comprises the steps of:

(1) knocking out the following three genes in *E. coli*: speA gene encoding an arginine decarboxylase, adiA gene encoding an arginine decarboxylase and astA gene encoding an arginine succinyltransferase;

(2) knocking out argE gene encoding an acetylornithine deacetylase in *E. coli*, and optionally integrating argJ gene encoding a glutamate acetyltransferase into *E. coli*;

(3) integrating the following arginine biosynthesis-related gene cluster: argG, argJ, argB, argD, argF, argG and argH, which was promoted by a $P_{trc}$ promoter;

(4) integrating pyrAA and pyrAB genes encoding a car-
    bamoyl phosphate synthetase;
(5) integrating lysE gene encoding an arginine transporter
    into the *E. coli* genome.

Those skilled in the art can understand that the order of
steps (1) to (5) of the above construction method of the
present invention is not limited, and can be performed in any
order that can be implemented by those skilled in the art.
Preferably, steps (1) to (5) are carried out in sequence.

Any gene knockout or gene silencing method known in
the art can be used to achieve the above-mentioned gene
knockout, and any method known in the art can also be used
to achieve gene integration, such as homologous recombi-
nation, overlap PCR, mutagenesis screening or gene editing
and other technologies. For example, gene knockout can be
achieved by removing a specific region from the gene so that
it does not have the function of expressing the protein of
interest, or by performing substitution, deletion and addition
of one or more nucleotides in the coding region or promoter
region by site-specific mutation, etc. and chemical reagents
can also be used to reduce or eliminate the transcription of
the specific gene.

In one embodiment, the construction method uses
CRISPR/Cas9-mediated gene editing technology to perform
gene integration and knockout.

In one embodiment, the construction method comprises
the steps of constructing a recombinant fragment and a
pGRB plasmid.

In one embodiment, the step of constructing the pGRB
plasmid comprises: designing a target sequence, preparing a
DNA fragment comprising the target sequence, and recom-
bining the DNA fragment comprising the target sequence
with a linearized vector fragment; in a specific embodiment,
the target sequence is 5'-NGG-3'.

In one embodiment, in the construction method, the step
of constructing a recombinant fragment comprises con-
structing a recombinant fragment for gene integration or for
gene knockout. Among them, the step of constructing a
recombinant fragment for gene integration comprises: using
the genome of the starting strain as a template, designing
primers for the upstream and downstream homologous arms
according to the upstream and downstream sequences of the
intended insertion site of the target gene, and designing
primers according to the target genome to amplify the target
gene fragment, and then performing overlap PCR to obtain
the recombinant fragment. The step of constructing a recom-
binant fragment for gene knockout comprises: using the
upstream and downstream sequences of the gene to be
knocked out as templates, designing primers for upstream
and downstream homologous arms; respectively amplifying
the upstream and downstream homologous arms by PCR,
and then preparing the recombinant fragment by overlap
PCR.

In one embodiment, the construction method comprises:
simultaneously transforming the pGRB plasmid and the
above-mentioned recombinant fragment into electropora-
tion-competent cells containing pREDCas9 and eliminating
plasmids, to obtain the recombinant genetically engineered
bacterial strain.

The present invention provides use of the above-men-
tioned genetically engineered bacterial strain in the prepa-
ration of L-arginine.

The present invention also provides a method for produc-
ing L-arginine by using the above-mentioned genetically
engineered bacterial strain, comprising: contacting the above-mentioned genetically engineered *E. coli* strain with
a fermentation medium, and conducting fermentation to
prepare L-arginine.

According to the present invention, the fermentation
includes shake flask fermentation or fermenter fermentation.

In one embodiment, the inoculum amount of shake flask
fermentation is 10-15%, the fermentation conditions are 37°
C., 200 r/min in a shaking table, the pH is maintained at
7.0-7.2 during the fermentation, and the pH can be adjusted
by adding ammonia water. During the fermentation, a glu-
cose solution can also be added to maintain the fermentation,
and the mass-volume concentration of the glucose solution
is preferably 60% (m/v). Preferably, the fermentation time of
the shake flask fermentation is 26-30 h. In the present
invention, the supplementary amount of the glucose solution
is not particularly limited, and the glucose concentration in
the fermentation broth can be maintained to be below 5 g/L,
for example, 1-5 g/L.

In one embodiment, the shake flask fermentation is per-
formed in a 500 mL erlenmeyer flask for fermentation. After
26-30 h shake flask fermentation, the concentration of
L-arginine in the fermentation broth can reach 30-32 g/L.

In one embodiment, the inoculum amount of fermenter
fermentation is 15-20%, the fermentation temperature is 35°
C., and the dissolved oxygen is between 25-35%. During the
fermentation, the pH is controlled to be stable between
7.0-7.2, and the pH can be adjusted by adding ammonia
water; when the glucose in the medium is exhausted, fed
batch addition of 80% (m/v) glucose solution is conducted
to maintain the glucose concentration in the fermentation
medium between 0.1-5 g/L.

In one embodiment, the fermenter fermentation is per-
formed in a 5 L fermenter for fermentation. After 50-55 h
fermentation in a 5 L fermenter, the accumulation of L-ar-
ginine reaches 130-135 g/L. The conversion rate reaches
0.48 g arginine/g glucose, and the production intensity
reaches 2.5 g arginine/L/h.

In the present invention, *E. coli* fermentation medium
known in the art can be used for fermentation.

In one embodiment, the fermentation medium for shake
flask fermentation is composed of: 20-40 g/L glucose, 1-3
g/L yeast extract, 2-3 g/L peptone, 3-6 g/L $K_2HPO_4$, 1-2 g/L
$MgSO_4.7H_2O$, 15-20 mg/L $FeSO_4.7H_2O$, 15-20 mg/L
$MnSO_4.7H_2O$, 1-3 mg/L each of $V_{B1}$, $V_{B3}$, $V_{B5}$, $V_{B12}$ and
$V_H$, the residual is water, pH 7.0-7.2.

In one embodiment, the fermentation medium for fer-
menter fermentation is composed of: 10-25 g/L glucose, 1-5
g/L yeast extract, 1-5 g/L peptone, 1-5 g/L $K_2HPO_4$, 1-3 g/L
$MgSO_4.7H_2O$, 10-30 mg/L $FeSO_4.7H_2O$, 10-30 mg/L
$MnSO_4H_2O$, 1-3 mg/L each of $V_{B1}$, $V_{B3}$, $V_{B5}$, $V_{B12}$ and Vu,
the residual is water, pH 7.0-7.2.

Beneficial Effects:

The present invention selected *E. coli* with short growth
cycle, clear metabolic pathway and convenient molecular
manipulation as the starting strain, starting from the genetic
engineering of L-arginine synthetic and metabolic pathway
and the engineering of the entire metabolic network, ana-
lyzed and reconstructed the metabolic flow related to argi-
nine in the L-arginine synthetic pathway and the entire
amino acid metabolic network and finally obtained a geneti-
cally engineered bacterial strain which has a clear genetic
background, carries no plasmids, undergoes no mutagenesis
and is capable of stably and efficiently producing L-arginine.

The *E. coli* strain obtained by the present invention
constructs the circulation path of L-arginine, improves the
flux of L-arginine and the supply of precursors, reduces the degradation of L-arginine, and promotes the accumulation and transport of L-arginine, thereby effectively increasing the yield of L-arginine.

The L-arginine-producing genetically engineered bacterial strain of the present invention can accumulate L-arginine of 130-135 g/L after being cultured in a 5 L fermenter for 50-55 h. The conversion rate can reach 0.48 g arginine/g glucose, and the production intensity can reach 2.5 g arginine/L/h. Compared with the strain reported by Park et al. (accumulation of L-arginine is 92.5 g/L after being cultured in a 5 L fermenter for 96 h, the conversion rate is 0.35 g arginine/g glucose, and the maximum production intensity is 0.9 g arginine/L/h), the present strain has the advantages of stronger L-arginine production capacity, without undergoing mutagenesis treatment, carrying no plasmid vectors, short fermentation cycle, clear genetic background, stable metabolism, high production intensity, and thus has good industrial application prospects.

DESCRIPTION OF THE DRAWINGS

In FIGS. 1(a) and 1(b), panel 1(a) shows the pREDCas9 plasmid map and panel 1(b) shows the pGRB plasmid map.

FIG. 2 shows the electropherogram of the construction and verification of the fragment for knocking out speA gene, wherein M: 1 kb DNA marker; lane 1: upstream homologous arm; lane 2: downstream homologous arm; lane 3: overlapping fragment; lane 4: original strain (control); lane 5: identified fragment from positive bacteria.

DETAILED DESCRIPTION OF THE INVENTION

Figure 3:
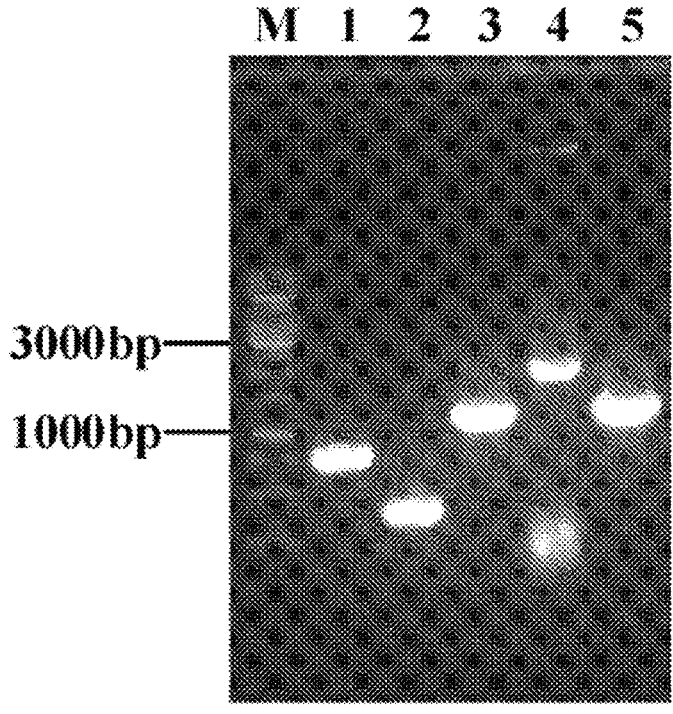
FIG. 3 shows the electropherogram of the construction and verification of the fragment for knocking out adiA gene, wherein M: 1 kb DNA marker; lane 1: upstream homologous arm; lane 2: downstream homologous arm; lane 3: overlapping fragment; lane 4: original strain (control); lane 5: identified fragment from positive bacteria.

The above and other characteristics and advantages of the present invention are explained and illustrated in more detail below by way of the description of the examples of the present invention. It should be understood that the following examples are meant to illustrate the technical solutions of the present invention, rather than to limit the protection scope of the present invention defined by the claims and their equivalent solutions.

Unless otherwise specified, the materials and reagents herein are commercially available, or can be prepared by those skilled in the art according to the prior art.

Example 1: Construction of Genetically Engineered Bacterial Strain E. coli TRP 05

1. Gene Editing Method

The gene editing method adopted in the present invention refers to literature "Li Y, Lin Z, Huang C, et al. Metabolic engineering of Escherichia coli using CRISPR-Cas9 mediated genome editing. Metabolic engineering, 2015, 31:13-21." and the maps of the two plasmids used in this method are shown in FIGS. 1(a) and 1(b). Among them, the pRED-Cas9 vector carries an elimination system of the gRNA expression plasmid pGRB, a Red recombination system of λ phage and a Cas9 protein expression system, spectinomycin resistance (working concentration: 100 mg/L), cultured at 32° C.; the pGRB vector uses pUC18 as the backbone and contains a promoter J23100, a gRNA-Cas9 binding domain sequence and a terminator sequence, ampicillin resistance (working concentration: 100 mg/L), cultured at 37° C.

The specific steps of this method:

1.1 Construction of pGRB Plasmid

The purpose of constructing the plasmid pGRB is to transcribe the corresponding gRNA to form a complex with Cas9 protein, and recognize the target site of the target gene through base pairing and PAM to achieve the target DNA double-strand break. The pGRB plasmid was constructed by recombining a DNA fragment containing the target sequence with a linearized vector fragment.

1.1.1 Design of the Target Sequence

CRISPR RGEN Tools was used to design the target sequence (PAM: 5'-NGG-3').

1.1.2 Preparation of the DNA Fragment Containing Target Sequence

The primer 5'-linearized vector end sequence (15 bp)-restriction site-target sequence (without PAM sequence)-linearized vector end sequence (15 bp)-3' and its reverse complementary primer were designed, and a DNA fragment comprising the target sequence was prepared by annealing of a single-stranded DNA. Reaction conditions: pre-denaturation at 95° C. for 5 min; annealing at 30-50° C. for 1 min. The annealing system was as follows:

TABLE 1

| Annealing system | |
| --- | --- |
| Reaction system | Volume (20 μL) |
| Primer (10 μmol/L) | 10 μL |
| Reverse complementary primer (10 μmol/L) | 10 μL |

1.1.3 Preparation of the Linearized Vector

The linearization of the vector adopted the method of inverse PCR amplification.

1.1.4 Recombination Reaction

The recombination system is shown in Table 2. The recombinases used were all enzymes of the ClonExpress® II One Step Cloning Kit series. Recombination conditions: 37° C., 30 min.

TABLE 2

| Recombination system | |
| --- | --- |
| Reaction system | Volume (10 μL) |
| 5 × CE II Buffer | 4 μL |
| Linearized clone vector | 1 μL |
| Inserted fragment clone vector | 1 μL |
| Exnase ® II | 2 μL |
| ddH₂O | 12 μL |

1.1.5 Plasmid Transformation

Ten μL of the reaction solution were added to 100 mL of DH5α chemically competent cells and mixed gently. The resulting mixture was cooled in an ice bath for 20 min, heated shock at 42° C. for 45-90 s, cooled immediately in an ice bath for 2-3 min, added with 900 μL of SOC, and recovered at 37° C. for 1 h. The mixture was centrifuged at 8,000 rpm for 2 min, part of the supernatant was discarded and the remaining 200 μL of the supernatant was used to resuspend the cells. The cells were then spread onto a plate containing 100 mg/L ampicillin, and the plate was placed upside down and cultured at 37° C. overnight. After single colonies were grown on the plate, positive recombinants were identified by colony PCR and picked.

1.1.6 Identification of Clones

The PCR-positive colonies were inoculated into LB medium containing 100 mg/L ampicillin for overnight culture, and the bacteria were preserved. The plasmids were extracted and identified by enzyme digestion.

1.2 Preparation of the Recombinant DNA Fragments

The recombinant fragment for knockout consists of the upstream and downstream homologous arms of the gene to be knocked out (upstream homologous arm-downstream homologous arm); the recombinant fragment for integration consists of the upstream and downstream homologous arms of the integration site and the gene fragment to be integrated (upstream homologous arm-target gene-downstream homologous arm). Using the primer design software primer5, the upstream and downstream sequences of the gene to be knocked out or the site to be integrated were used as the template to design the primers for the upstream and downstream homologous arms (amplification product length: about 400-500 bp); the gene to be integrated was used as the template to design the primers for the amplification of the integrated gene. After amplifying the upstream and downstream homologous arms and the target gene fragment by PCR, respectively, the recombinant fragment was prepared by overlap PCR. The PCR system and method are shown in the following Table 3:

TABLE 3

| PCR amplification system | |
| --- | --- |
| Component | Volume (50 μL) |
| DNA template | 1 μL |
| Forward primer (10 μmol/L) | 1 μL |
| Reverse primer (10 μmol/L) | 1 μL |
| dNTP mixture (10 mmol/L) | 4 μL |
| 5 × Buffer | 10 μL |
| HS enzyme (5 U/μL) | 0.5 μL |
| ddH₂O | 32.5 μL |

The overlap PCR system is shown in the following Table 4:

TABLE 4

| Overlap PCR amplification system | |
| --- | --- |
| Component | Volume (50 μL) |
| Template | 2 μL |
| Forward primer for the upstream homologous arm (10 μmol/L) | 1 μL |
| Reverse primer for the downstream homologous arm (10 μmol/L) | 1 μL |
| dNTP mixture (10 mmol/L) | 4 μL |
| 5 × Buffer | 10 μL |
| HS enzyme (5 U/μL) | 0.5 μL |
| ddH₂O | 31.5 μL |

PCR reaction conditions (PrimeSTAR HS enzyme from Takara Bio): pre-denaturation at 95° C. for 5 min; 30 cycles of denaturation at 98° C. for 10 s, annealing at (Tm-3/5° C.) for 15s, extension at 72° C.; and a final extension at 72° C. for 10 min; hold at 4° C.

1.3 Transformation of Plasmids and the Recombinant DNA Fragment 1.3.1 Transformation of pREDCas9

The pREDCas9 plasmid was electro-transformed into the electroporation-competent cells of W3110 by electro-transformation. The cells were recovered and cultured and then spread on a LB plate containing spectinomycin, and cultured at 32° C. overnight. Single colonies grown on the plate with the antibiotic were subjected to colony PCR with identification primers to screen positive recombinants.

1.3.2 Preparation of Electroporation-Competent Cells of the Target Strain Containing pREDCas9

The strain was cultured at 32° C. until the culture reached an OD600 of from 0.1 to 0.2, and then IPTG was added (to a final concentration of 0.1 mM). The culture was continued until OD600 value reached from 0.6 to 0.7. The obtained cells were used for the preparation of competent cells. The purpose of adding IPTG is to induce the expression of the recombinase on the pREDCas9 plasmid. The medium and preparation process required for the preparation of the competent cells refer to conventional standard operations.

1.3.3 Transformation of pGRB and the Recombinant DNA Fragment

The pGRB plasmid and the recombinant DNA fragment were simultaneously electro-transformed into the electroporation-competent cells containing pREDCas9. After electro-transformation, the cells were recovered and cultured and then spread on a LB plate containing ampicillin and spectinomycin, and cultured at 32° C. overnight. Colony PCR verification was performed by using the forward primer for the upstream homologous arm and the reverse primer for the downstream homologous arm, or by using specifically designed primers for identification, to screen positive recombinants and the recombinants were preserved.

1.4 Elimination of Plasmids 1.4.1 Elimination of Plasmid pGRB

The positive recombinant was cultured overnight in LB medium containing 0.2% arabinose, and after appropriate dilutions, the culture was spread on a LB plate containing spectinomycin, and cultured at 32° C. overnight. The obtained recombinants were then inoculated into LB plates containing ampicillin and spectinomycin, respectively, and single colonies that did not grow on the plate containing ampicillin but grew on the plate containing spectinomycin were picked and preserved.

1.4.2 Elimination of Plasmid pREDCas9

The positive recombinant was transferred to LB liquid medium without antibiotics, cultured overnight at 42° C., and after appropriate dilutions, the culture was spread on a LB plate without antibiotics and cultured at 37° C. overnight. The obtained recombinants were then inoculated into LB plates containing spectinomycin and without antibiotics, respectively, single colonies that did not grow on the plate with spectinomycin but grew on the LB plate without antibiotics were picked and preserved.

2. The primers used in the strain construction are shown in Table 5:

TABLE 5

Primers used in the strain construction

| Primer | Sequence (5'-3') |
|---|---|
| UP-speA-S | TTAACCTGTCTCACCGTTCTGG (SEQ ID NO: 1) |
| UP-speA-A | ACAAACCTGCCTCGAACTCTTCCGC TGACGAAGGCAAACC (SEQ ID NO: 2) |
| DN-speA-S | GGTTTGCCTTCGTCAGCGGAAGAGT TCGAGGCAGGTTTGT (SEQ ID NO: 3) |
| DN-speA-A | CATATACCAGATCGCCGCAGT (SEQ ID NO: 4) |
| UP-adiA-S | CGAGTTTCTCCATCAAGACACCT (SEQ ID NO: 5) |
| UP-adiA-A | CGCCCATAGAGAACAGGAACATGCG GGTTGGCACCATATA (SEQ ID NO: 6) |

TABLE 5-continued

Primers used in the strain construction

| Primer | Sequence (5'-3') |
|---|---|
| DN-adiA-S | TATATGGTGCCAAGCCGCATGTTCC TGTTCTCTATGGGCG (SEQ ID NO: 7) |
| DN-adiA-S | TATCGCCGAAGTTTTCACCAG (SEQ ID NO: 8) |
| UP-astA-S | GGCACTCATGGCACCACCT (SEQ ID NO: 9) |
| UP-astA-A | TGAGGGCATCCAGTTGTGCCTGCAT CAGCGCCGAGAC (SEQ ID NO: 10) |
| DN-astA-S | GTCTCGGCGCTGATGCAGGCACAAC TGGATGCCCTCA (SEQ ID NO: 11) |
| DN-astA-A | TGACCAGGGAAATTATACGGC (SEQ ID NO: 12) |
| UP-argE-S | GCCCGCTTCAAGAAACTGC (SEQ ID NO: 13) |
| UP-argE-A | AATTGTTATCCGCTCACAATTCCAC ACATTATACGAGCCGGATGATTAAT TGTCAAGGCGCTTATTGAAGGTGTG G (SEQ ID NO: 14) |
| argJ-S | TCCGGCTGGTATAAGTGTGGAATTG TGAGCGGATAACAATTTCACACAGG AAACAGACGATGGCAGAAAAAGGCA TTACC (SEQ ID NO: 15) |
| argJ-A | GTTGATGAGCCTGATTAATTGAGCG CCCTTTTCCCTGCTTGTTAG (SEQ ID NO: 16) |
| DN-argE-S | CTAACAAGCAGGGAAAAGGGCGCTC AATTAATCAGGCTCATCAAC (SEQ ID NO: 17) |
| DN-argE-A | CTGTATCCTTCACGTCGCATTG (SEQ ID NO: 18) |
| UP-yghX-S | GCGCAACGTAGAACAGGAATT (SEQ ID NO: 19) |
| UP-yghX-A | AATTGTTATCCGCTCACAATTCCAC ACATTATACGAGCCGGATGATTAAT TGTCAAGATTGAAGCGCCTTTACTA CTCC (SEQ ID NO: 20) |
| argC-argJ-S | TCCGGCTCGTATAATGTGTGGAATT GTGAGCGGATAACAATTTCACACAG GAAACAGACCATGATCATGCATAAC GTGTATGGTG (SEQ ID NO: 21) |
| argC-argJ-A | GCCCCAAGGGGTTATGCTAGCCTAC AAATTGAGTTATGTTC ATTTAAATATGATGTTGTTCAGTTA AGAGCTGTACGCGCAGTTGA (SEQ ID NO: 22) |
| DN-yghX-S1 | CTGAACAACATCATATTTAAATGAA CATAACTCAATTTGTAGGCTAGCAT AACCCCTTGGGGCGTCATAGTAATC CAGCAACTCTTCTG (SEQ ID NO: 23) |
| DN-yghX-A | GAGCAGGTATTTACGTGAACCG (SEQ ID NO: 24) |

TABLE 5-continued

Primers used in the strain construction

| Primer | Sequence (5'-3') |
|---|---|
| UV-argB-argD-argF-S | GTACGCAGCTTGTTCTGATATCG (SEQ ID NO: 25) |
| UP-argB-argD-argF-A | AGTTGCTGGATTACTATGACCCTAG AAGAAATCAACCAGCGCATCAGAAA GTCTCCTGTGCATTTACCTCGGCTG GTTGGC (SEQ ID NO: 26) |
| DN-yghX-S2 | ATGCACAGGAGACTTTCTGATGCGC TCGTTGATTTCTTCTAGCGTCATAG TAATCCAGCAACTCTCATAGTAATC CAGCAACTCTTGTG (SEQ ID NO: 27) |
| UP-argG-argH-S | GATATTTCCATCATCGCTCCTG (SEQ ID NO: 28) |
| UP-argG-argH-A | CTCGGGTTATACCTTACCTGCCTTA CCTCGGCTGGTTGGC (SEQ ID NO: 29) |
| argG-argH-S | GCCAACCAGCCGAGGTAAGGCAGGT AAGGTATAACCCGAG (SEQ ID NO: 30) |
| argG-argH-A | CACCGACAAACAACAGATAAAACGA AAGGCCCAGTCTTTCGACTGAGCCT TTCGTTTTATTTGTTATCGACGTAC CCCCGC (SEQ ID NO: 31) |
| DN-yghX-S3 | AAAGACTGGGCCTTTCGTTTTATCT GTTGTTTGTCGGTGAACGCTCTCCT GAGTAGGACAAATGTCATAGTAATC CAGCAACTCTTGTG (SEQ ID NO: 32) |
| UP-yjiT-S | AATAGTTGTTGCCGCCTGAGT (SEQ ID NO: 33) |
| UP-yjiT-A | AATTGTTATCCGCTCACAATTCCAC ACATTATACGAGCCGGATGATTAAT TGTCAAAAAACAGGCAGCAAAGTCC C (SEQ ID NO: 34) |
| 1-PyrAA-pyrAB-S | TCCGGCTCGTATAATGTGTGGAATT GTGAGCGGATAACAATTTCACACAG GAAACAGACCATGAAGAGACGATTA GTACTGGAAAAC (SEQ ID NO: 35) |
| 1-PyrAA-pyrAB-A | GCCCCAAGGGGTTATGCTAGCCTAC AAATTGAGTTATGTTCATTTAAATA TGATGTTGTTCAGAGAAGACATCGA TAGCGGAAAAT (SEQ ID NO: 36) |
| DN-yjiT-S | CTGAACAACATCATATTTAAATGAA CATAACTCAATTTGTAGGCTAGCAT AACCCCTTGGGGCAAGCACTACCTG TGAAGGGATGT (SEQ ID NO: 37) |
| DN-yjiT-A | CAGGGTTTCCACAGTCACAAT (SEQ ID NO: 38) |
| 2-PyrAA-pyrA B-S | ACCCGGTGACAGGAAAAACAT (SEQ ID NO: 39) |

TABLE 5-continued

Primers used in the strain construction

| Primer | Sequence (5'-3') |
|---|---|
| 2-PyrAA-pyrA B-A | CACCGACAAACAACAGATAAAACGA AAGGCCCAGTCTTTCGACTGAGCCT TTCGTTTTATTTGTCATATAGTGAC TGCCGCCTCC (SEQ ID NO: 40) |
| DN-yjiT-S1 | AAAGACTGGGCCTTTCGTTTTATCT GTTGTTTGTCGGTGAACGCTCTCCT GAGTAGGACAAATAAGCACTACCTG TGAAGGGATGT (SEQ ID NO: 41) |
| UP-ilvG-S | ACCGAGGAGCAGACAATGAATAA (SEQ ID NO: 42) |
| UP-ilvG-A | AATTGTTATCCGCTCACAATTCCAC ACATTATACGAGCCGGATGATTAAT TGTCAAGGTGATGGCAACAACAGGG A (SEQ ID NO: 43) |
| lysE-S | TCCGGCTCGTATAATGTGTGGAATT GTGAGCGGATAACAATTTCACACAG GAAACAGACCATGGAAATTTTCGTT ACGGGTC (SEQ ID NO: 44) |
| lysE-A | CACCGACAAACAACAGATAAAACGA AAGGCCCAGTCTTTCGACTGAGCCT TTCGTTTTATTTGTTAGCCCATCAG AATCAGTTTCAC (SEQ ID NO: 45) |
| DN-ilvG-S | AAAGACTGGGCCTTTCGTTTTATC TGTTGTTTGTCGGTGAACGCTCTCC TGAGTAGGACAAATCTATCTACGCG CCGTTGTTGT (SEQ ID NO: 46) |
| DN-ilvG-A | GCGCTGGCTAACATGAGGAA (SEQ ID NO: 47) |
| gRNA-speA-S | AGTCCTAGGTATAATACTAGTTGCG TACTTACAATATTGCCGTTTTAGAG CTAGAA (SEQ ID NO: 48) |
| gRNA-speA-A | TTCTAGCTCTAAAACGGCAATATTG TAAGTACGCAACTAGTATTATACCT AGGACT (SEQ ID NO: 49) |
| gRNA-adiA-S | AGTCCTAGGTATAATACTAGTTATC GGGCCAATCTATCCGCGTTTTAGAG CTAGAA (SEQ ID NO: 50) |
| gRNA-adiA-A | TTCTAGCTCTAAAACGCGGATAGAT TGGCCCGATAACTAGTATTATACCT AGGACT (SEQ ID NO: 51) |
| gRNA-astA-S | AGTCCTAGGTATAATACTAGTTCTC TGCGGCACCGGGCAAAGTTTTAGAG CTAGAA (SEQ ID NO: 52) |
| gRNA-astA-A | TTCTAGCTCTAAAACTTTGCCCGGT GCCGCAGAGAACTAGTATTATACCT AGGACT (SEQ ID NO: 53) |
| gRNA-argE-S | AGTCCTAGGTATAATACTAGTTCA GATTTAATCACTCTGCGTTTTAGAG CTAGAA (SEQ ID NO: 54) |

TABLE 5-continued

Primers used in the strain construction

| Primer | Sequence (5'-3') |
|---|---|
| gRNA-argE-A | TTCTAGCTCTAAAACGCAGAGTGAT TAAATCTGCAACTAGTATTATACCT AGGACT (SEQ ID NO: 55) |
| gRNA-yghX-S | AGTCCTAGGTATAATACTAGTGGTG CCTGACGACCATAAAAGTTTTAGAG CTAGAA (SEQ ID NO: 56) |
| gRNA-yghX-A | TTCTAGCTCTAAAACTTTTATGGTC GTCAGGCACCACTAGTATTATACCT AGGACT (SEQ ID NO: 57) |
| gRNA-argBDF-S | CTGAACAACATCATATTTAAATGAA CATAACTCAATTTGTAGGCTAGCAT AACCCCTTGGGGC (SEQ ID NO: 58) |
| gRNA-argBDF-A | GCCCCAAGGGGTTATGCTAGCCTAC AAATTGAGTTATGTTCATTTAAATA TGATGTTGTTCAGTTAAGAGCTGTA CGCGGAGTTGA (SEQ ID NO: 59) |
| gRNA-argG-argH-S | ATGCACAGGAGACTTTCTGATGCGC TGGTTTCATTTCTTCTAGGGTCATA GTAATCCAGCAACT (SEQ ID NO: 60) |
| gRNA-argG-argH-A | AGTTCCTGGATTACTATCACCCTAC AAGAAATCAACCAGCCCATCAGAAA GTCTCCTGTGCAT (SEQ ID NO: 61) |
| gRNA-yjiT-S | AGTCCTAGGTATAATACTAGTAGGG ATTATGAACGGCAATGGTTTTAGAG CTAGAA (SEQ ID NO: 62) |
| gRNA-yjiT-A | TTCTAGCTCTAAAACCATTGCCGTT CATAATCCCTACTAGTATTATACCT AGGACT (SEQ ID NO: 63) |
| gRNA-pyrAA-pyrAB-S | CTGAACAACATCATATTTAAATGAA CATAACTCAATTTGTAGGCTAGCAT AACCCCTTGGGGC (SEQ ID NO: 64) |
| gRNA-pyrAA-pyrAB-A | GCCCCAAGGGGTTATGCTAGCCTAC AAATTGAGTTATGTTCATTTAAATA TGATG1TGTTCAG (SEQ ID NO: 65) |
| gRNA-ilvG-S | AGTCCTAGGTATAATACTAGTGGAA GAGTTGCCGCGCATCAGTTTTAGAG CTAGAA (SEQ ID NO: 66) |
| gRNA-ilvG-A | TTCTAGCTCTAAAACTGATGCGCGG CAACTCTTCCACTAGTATTATACCT AGGACT (SEQ ID NO: 67) |

3. Specific Process of Strain Construction 3.1 Knockout of the three genes, speA, adiA and astA 3.1.1 Knockout of speA gene Using *E. coli* W3110 (ATCC27325) genome as the template, PCR was performed with the primers for the upstream homologous arm (UP-speA-S, UP-speA-A) and the primers for the downstream homologous arm (DN-speA-S, DN-speA-A) designed according to the upstream and downstream sequences of its speA gene (NCBI-GeneID: 12933352) to amplify the upstream and downstream homologous arms of the speA gene. The overlap PCR method was applied to fuse the above fragments to obtain a fragment for knocking out speA gene (upstream homologous arm-downstream homologous arm). The DNA fragment obtained by annealing primers gRNA-speA-S and gRNA-speA-A was ligated with the plasmid pGRB to construct a recombinant plasmid pGRB-spe.A. *E. coli* W3110 competent cells were prepared, according to the methods described in sections 1.3 and 1.4. The plasmid pGRB-speA and the fragment for knocking out speA gene were electro-transformed into the competent cells at the same time, and finally a strain named *E. coli* W3110 ARG1 was obtained. The electropherogram of the construction of the fragment for knocking out speA gene and the PCR verification of the positive bacteria was shown in FIG. 2, wherein, the length of the upstream homologous arm should be 397 bp, the length of the downstream homologous arm should be 468 bp, and the full length of the overlapping fragment should be 865 bp, and for PCR verification, the length of the PCR amplified fragment of the positive bacteria should be 2752 bp, and the length of the PCR amplified fragment of the original bacteria should be 865 bp.

3.1.2 Knockout of adiA gene

Using *E. coli* W3110 (ATCC27325) genome as the template, PCR was performed with the primers for the upstream homologous arm (UP-adiA-S, UP-adiA-A) and the primers for the downstream homologous arm (DN-adiA-S, DN-adiA-A) designed according to the upstream and downstream sequences of its adiA gene (NCBI-GeneID: 12934085) to amplify the upstream and downstream homologous arms of the adiA gene. The overlap PCR method was applied to fuse the above fragments to obtain a fragment for knocking out adiA gene (upstream homologous arm-downstream homologous arm). The DNA fragment obtained by annealing primers gRNA-adiA-S and gRNA-adiA-A was ligated with the plasmid pGRB to construct a recombinant plasmid pGRB-adiA. *E. coli* W3110 ARG1 competent cells were prepared, according to the methods described in sections 1.3 and 1.4. The plasmid pGRB-adiA and the fragment for knocking out adiA gene were electro-transformed into the competent cells at the same time, and finally a strain named *E. coli* W3110 ARG2 was obtained. The electropherogram of the construction of the fragment for knocking out adiA gene and the PCR verification of the positive bacteria was shown in FIG. 3, wherein, the length of the upstream homologous arm should be 806 bp, the length of the downstream homologous arm should be 402 bp, and the full length of the overlapping fragment should be 1208 bp, and for PCR verification, the length of the PCR amplified fragment of the positive bacteria should be 2124 bp, and the length of the PCR amplified fragment of the original bacteria should be 1208 bp.

3.1.3 Knockout of astA gene

Figure 4:
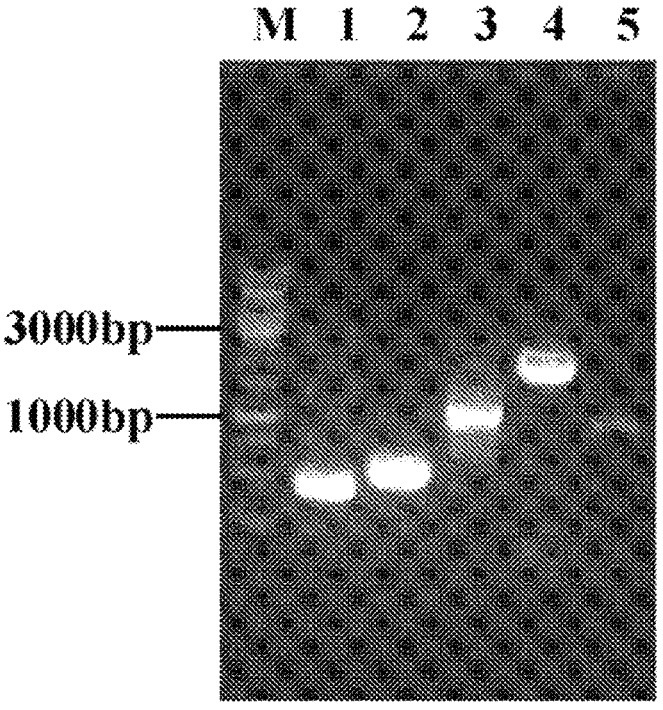
FIG. 4 shows the electropherogram of the construction and verification of the fragment for knocking out astA gene, wherein M: 1 kb DNA marker; lane 1: upstream homologous arm; lane 2: downstream homologous arm; lane 3: overlapping fragment; lane 4: original strain (control); lane 5: identified fragment from positive bacteria.

Using *E. coli* W3110 (ATCC27325) genome as the template, PCR was performed with the primers for the upstream homologous arm (UP-astA-S, UP-astA-A) and the primers for the downstream homologous arm (DN-astA-S, DN-astA-A) designed according to the upstream and downstream sequences of its adiA gene (NCBI-GeneID: 12933241) to amplify the upstream and downstream homologous arms of the astA gene. The overlap PCR method was applied to fuse the above fragments to obtain a fragment for knocking out astA gene (upstream homologous arm-downstream homologous arm). The DNA fragment obtained by annealing primers gRNA-astA-S and gRNA-astA-A was ligated with the plasmid pGRB to construct a recombinant plasmid pGRB-astA. *E. coli* W3110 ARG2 competent cells were prepared, according to the methods described in sections 1.3 and 1.4. The plasmid pGRB-astA and the fragment for knocking out astA gene were electro-transformed into the competent cells at the same time, and finally a strain named *E. coli* W3110 ARG3 was obtained. The electropherogram of the construction of the fragment for knocking out astA gene and the PCR verification of the positive bacteria was shown in FIG. 4, wherein, the length of the upstream homologous arm should be 443 bp, the length of the downstream homologous arm should be 523 bp, and the full length of the overlapping fragment should be 965 bp, and for PCR verification, the length of the PCR amplified fragment of the positive bacteria should be 1869 bp, and the length of the PCR amplified fragment of the original bacteria should be 965 bp.

Figure 5:
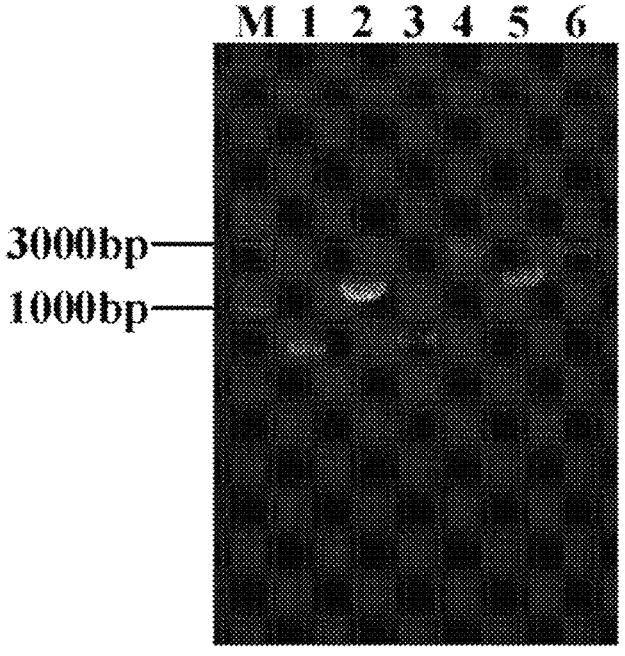
FIG. 5 shows the electropherogram of the construction and verification of the fragment for integrating argJ gene, wherein M: 1 kb DNA marker; lane 1: upstream homologous arm; lane 2: downstream homologous arm; lane 3: overlapping fragment; lane 4: original strain (control); lane 5: identified fragment from positive bacteria.

3.2 Knockout the argE Gene in *E. coli* and Integration of the argJ Gene from *Corynebacterium glutamicum* at this Locus Using *E. coli* W3110 (ATCC27325) genome as the template, PCR was performed with the primers for the upstream homologous arm (UP-argE-S, UP-argE-A) and the primers for the downstream homologous arm (DN-argE-S, DN-argE-A) designed according to the upstream and downstream sequences of its argE gene (NCBI-GeneID: 12930574) to amplify the upstream and downstream homologous arms of the argE gene. Using *Corynebacterium glutamicum* (ATCC13032) genome as the template, PCR was performed with the primers (argJ-S, argJ-A) designed according to its argJ gene sequence (NCBI-GeneID: 1019371) to amplify the argJ fragment; promoter Pirc was designed in the reverse primer for the upstream homologous arm and the forward primer for the argJ gene. The overlap PCR method was applied to fuse the above fragments to obtain a fragment for knocking out argE gene and integrating argJ gene (upstream homologous arm-P$_{trc}$-argJ-downstream homologous arm). The DNA fragment obtained by annealing primers gRNA-argE-S and gRNA-argE-A was ligated with the plasmid pGRB to construct a recombinant plasmid pGRB-argE. *E. coli* W3110 ARG3 competent cells were prepared, according to the methods described in sections 1.3 and 1.4. The plasmid pGRB-argE and the fragment for knocking out argE gene and integrating arg/gene were electro-transformed into the competent cells at the same time, and finally a strain named *E. coli* W3110 ARG4 was obtained. The electropherogram of the construction of the fragment for integration and the PCR verification of the positive bacteria during the Pure-argJ fragment integration process was shown in FIG. 5, wherein, the length of the upstream homologous arm should be 510 bp, the length of the argJ gene should be 1206 bp, the length of the downstream homologous arm should be 668 bp, and the full length of the overlapping fragment should be 2458 bp, and for the PCR verification of the recombinants, the length of the amplified fragment of the positive recombinants should be 2458 bp, and the length of the amplified fragment of the original bacteria should be 2154 bp.

3.2 Integration of the Arginine Synthesis Operon from *Corynebacterium glutamicum* into the yghX Gene Locus in *E. coli*

The arginine synthesis operator gene from *Corynebacterium glutamicum* (containing seven genes, argC, argJ, argB, argD, argF, argG and argH) were successively integrated into the yjhX gene locus in *E. coli*, and the transcription and expression of this foreign operon was initiated by a promoter Pure, and finally the strain named *E. coli* W3110 ARG7 was constructed.

The integration of arginine synthesis operator gene from *Corynebacterium glutamicum* is divided into three stages.

3.2.1 Integration of Pre-argC-argJ

Figure 6:
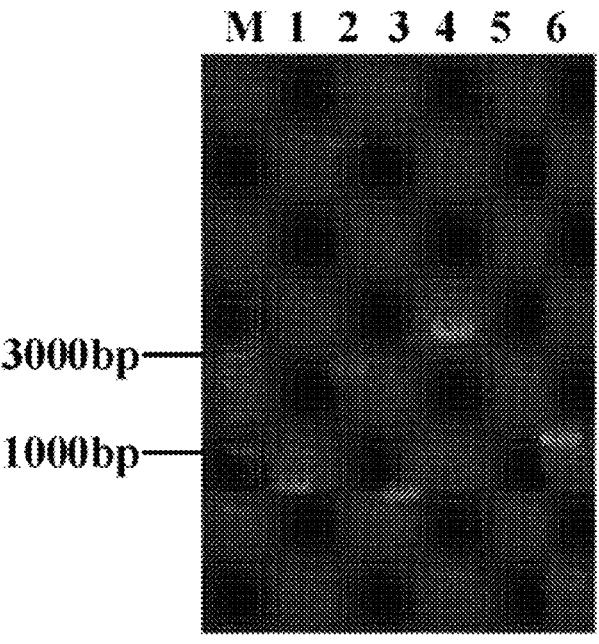
FIG. 6 shows the electropherogram of the construction and verification of the fragment for integrating argC-arg), wherein M: 1 kb DNA marker; lane 1: upstream homologous arm; lane 2: argC-argJ fragment; lane 3: downstream homologous arm; lane 4: overlapping fragment; lane 5: original strain (control); lane 6: identified fragment from positive bacteria.

Using *E. coli* W3110 (ATCC27325) genome as the template, PCR was performed with the primers for the upstream homologous arm (UP-yghX—S, UP-yghX-A) and the primers for the downstream homologous arm (DN-yghX-S1, DN-yghX-A) designed according to the upstream and downstream sequences of its yghX gene to amplify the upstream and downstream homologous arms of the yghX gene. Using *Corynebacterium glutamicum* (ATCC13032) genome as the template, PCR was performed with the primers (argC-argJ-S, argC-argJ-A) designed according to its argC-argJ gene sequences (NCBI-GeneID: 1019370, 1019371) to amplify the argC-argJ fragment; promoter Pirc was designed in the reverse primer for the upstream homologous arm and the forward primer for the argC-argJ gene. The overlap PCR method was applied to fuse the above fragments to obtain a fragment for integrating argC-argJ genes (upstream homologous arm-P$_{trc}$-argC-argJ-downstream homologous arm). The DNA fragment containing the target sequence was obtained by annealing primers gRNA-yghX-S and gRNA-yghX-A, and then ligated with the plasmid pGRB to construct a recombinant plasmid pGRB-yghX. *E. coli* W3110 ARG4 competent cells were prepared, according to the methods described in sections 1.3 and 1.4. The plasmid pGRB-yghX and the fragment for integrating argC-argJ genes were electro-transformed into the competent cells at the same time, and finally a strain named *E. coli* W3110 ARG5 was obtained. The electropherogram of the construction of the fragment for integration and the PCR verification of the positive bacteria during the Pic-argC-argJ fragment integration process was shown in FIG. 6, wherein, the length of the upstream homologous arm should be 602 bp, the length of the argC-argJ gene fragment should be 2324 bp, the length of the downstream homologous arm should be 561 bp, and the full length of the overlapping fragment should be 3650 bp, and the length of the amplified fragment by using the identification primers should be 1068 bp, and no bands should be amplified from the original bacteria.

3.2.2 Integration of argB-argD-argF

Figure 7:
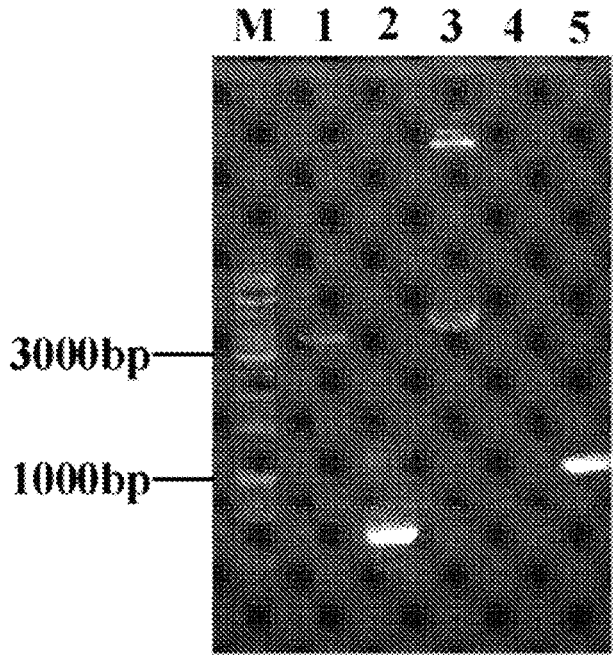
FIG. 7 shows the electropherogram of the construction and verification of the fragment for integrating argB-argD-argF, wherein M: 1 kb DNA marker; lane 1: argB-argD-argF upstream fragment-argB-argD-argF gene fragment; lane 2: downstream homologous arm; lane 3: overlapping fragment; lane 4: original strain (control); lane 5: identified fragment from positive bacteria.

Using *Corynebacterium glutamicum* (ATCC13032) genome as the template, PCR was performed with the primers for the upstream homologous arm (UP-argB-argD-argF-S, UP-argB-argD-argF-A) designed according to the argB-argD-argF genes (NCBI-GeneID: 1019372, 1019373, 1019374) and their upstream sequence to amplify the upstream homologous arm of the argB-argD-argF genes. Using *E. coli* W3110 (ATCC27325) genome as the template, PCR was performed with the primers for the downstream homologous arm (DN-yghX-S2, DN-yghX-A) designed according to the downstream sequence of its yghX gene to amplify the downstream homologous arm of the yghX gene. The overlap PCR method was applied to fuse the above fragments to obtain a fragment for integrating argB-argD-argF genes (argB upstream fragment-argB-argD-argF-downstream homologous arm). The DNA fragment containing the target sequence was obtained by annealing primers gRNA-argBDF-S and gRNA-argBDF-A, and then ligated with the plasmid pGRB to construct a recombinant plasmid pGRB-argBDF. *E. coli* W3110 ARG5 competent cells were prepared, according to the methods described in sections 1.3 and 1.4. The plasmid pGRB-argBDF and the fragment for integrating argB-argD-argF genes were electro-transformed into the competent cells at the same time, and finally a strain named *E. coli* W3110 ARG6 was obtained. The electropherogram of the construction of the fragment for integration and the PCR verification of the positive bacteria during the argB-argD-argF fragment integration process was shown in FIG. 7, wherein, the full length of the argB upstream fragment-argB-argD-argF was 3575 bp, the length of the downstream homologous arm was 561 bp, and the length of the overlapping fragment was 4219 bp, and the length of the fragment amplified by the identification primers was 1034 bp, and no bands should be amplified from the original bacteria.

3.2.3 Integration of argG-argH

Figure 8:
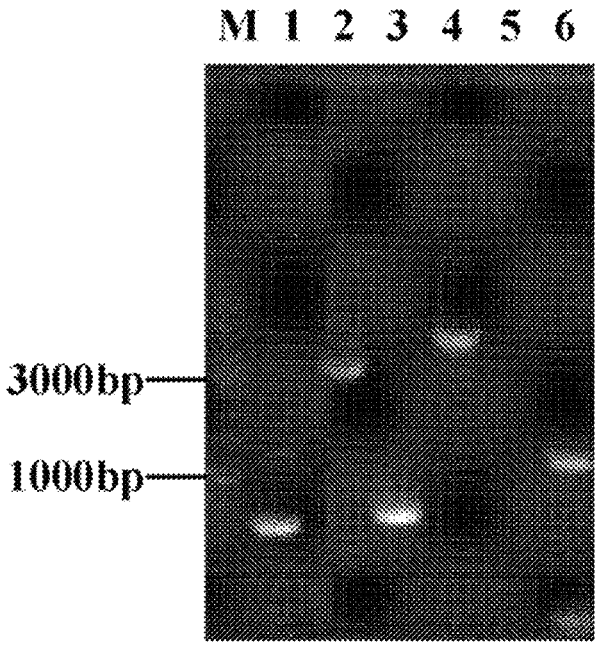
FIG. 8 shows the electropherogram of the construction and verification of the fragment for integrating argG-argH, wherein M: 1 kb DNA marker; lane 1: upstream homologous arm; lane 2: argG-argH fragment; lane 3: downstream homologous arm; lane 4: overlapping fragment; lane 5: original strain (control); lane 6: identified fragment from positive bacteria.

Using *Corynebacterium glutamicum* (ATCC13032) genome as the template, PCR was performed with the primers for the upstream homologous arm (UP-argG-argH—S, UP-argG-argH-A) and the primers for the argG-argH fragment (argG-argH-S, argG-argH-A) designed according to argG-argH (NCBI-GeneID: 1019376, 1019377) and their upstream sequence to amplify the upstream homologous arm of the argG-argH genes and the argG-argH fragment. Using *E. coli* W3110 (ATCC27325) genome as the template, PCR was performed with the primers for the downstream homologous arm (DN-yghX-S3, DN-yghX-A) designed according to the downstream sequence of its yghX gene to amplify the downstream homologous arm of the yghX gene. The overlap PCR method was applied to fuse the above fragments to obtain a fragment for integrating argG-argH genes (argG upstream fragment-argG-argH-downstream homologous arm). The DNA fragment containing the target sequence was obtained by annealing primers gRNA-argG-argH-S and gRNA-argG-argH-A, and then ligated with the plasmid pGRB to construct a recombinant plasmid pGRB-argG-argH. *E. coli* W3110 ARG6 competent cells were prepared, according to the methods described in sections 1.3 and 1.4. The plasmid pGRB-argG-argH and the fragment for integrating argG-argH genes were electro-transformed into the competent cells at the same time, and finally a strain named *E. coli* W3110 ARG7 was obtained. The electropherogram of the construction of the fragment for integration and the PCR verification of the positive bacteria during the argG-argH fragment integration process was shown in FIG. 8, wherein, the full length of the argG upstream fragment was 405 bp, the full length of the argG-argH fragment was 2826 bp, the length of the downstream homologous arm was 561 bp, and the length of the overlapping fragment should be 3875 bp, and the length of the fragment amplified by the identification primers should be 1521 bp, and no bands should be amplified from the original bacteria.

3.3 Integration of the pyrAA-pyrAB Genes from *B. subtilis* into the yjiT Gene Locus of *E. coli*

*B. subtilis* A260 was bred from *B. subtilis* 168 as the starting strain by combining ARTP mutagenesis and high-throughput screening (this strain was deposited on Dec. 2, 2015 at China General Microbiological Culture Collection Center (Address: Institute of Microbiology, Chinese Academy of Sciences, No. 1 West Beichen Road, Chaoyang District, Beijing, Postcode: 100101) with a deposition number of CGMCC No. 11775). The strain relieved the feedback regulation of uridylic acid and arginine on the carbamyl phosphate synthetase, and by sequencing the pyrimidine nucleotide operon gene, it was found that the glutamic acid residue at position 949 was deleted from the large subunit of carbamyl phosphate (encoded by pyrAB) (publication number: CN105671007A). The carbamyl phosphate synthetase genes (pyrAA, pyrAB) in *B. subtilis* A260 without feedback inhibition of arginine were integrated into *E. coli* to improve the supply of the precursor carbamyl phosphate in the process of arginine synthesis.

The pyrAA-pyrAB gene fragment of 4292 bp in length from *B. subtilis* was integrated into *E. coli* in two segments, wherein the first segment was 2651 bp and the second segment was 1641 bp.

3.3.1 Integration of the First Segment Pure-pyrAA-pyrAB

Figure 9:
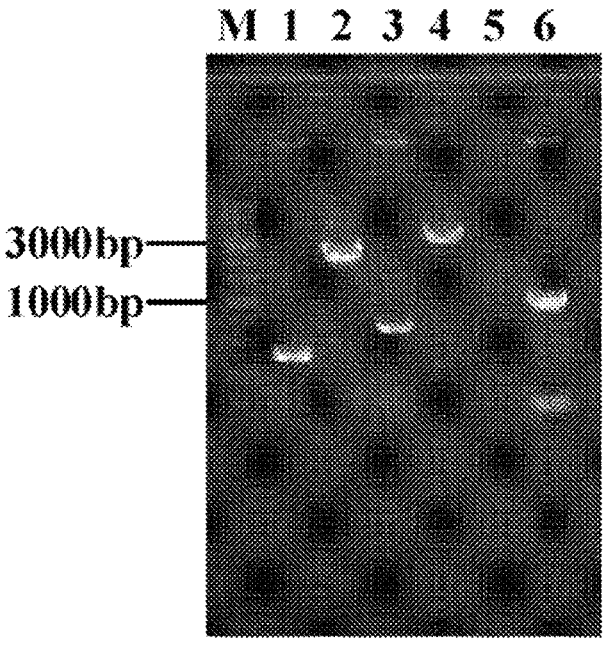
FIG. 9 shows the electropherogram of the construction and verification of the first fragment for integrating pyrAA-pyrAB, wherein M: 1 kb DNA marker; lane 1: upstream homologous arm; lane 2:1-pyrAA-pyrAB fragment; lane 3: downstream homologous arm; lane 4: overlapping fragment; lane 5: original strain (control); lane 6: identified fragment from positive bacteria.

Using *E. coli* W3110 (ATCC27325) genome as the template, PCR was performed with the primers for the upstream homologous arm (UP-yjiT-S, UP-yjiT-A) and the primers for the downstream homologous arm (DN-yjiT-S, DN-yjiT-A) designed according to the upstream and downstream sequences of its yjiT gene to amplify the upstream and downstream homologous arms of the yjiT gene. Using *B. subtilis* (CGMCC No. 11775) genome as the template, PCR was performed with the primers (1-pyrAA-pyrAB-S, 1-pyrAA-pyrAB-A) designed according to pyrAA gene (NCBI-GeneID: 937368) and pyrAB gene (NCBI-GeneID: 936608) to amplify the first segment pyrAA-pyrAB gene fragment. Promoter Pire was designed in the reverse primer for the upstream homologous arm and the forward primer for the pyrAA-pyrAB genes. The overlap PCR method was applied to fuse the above fragments to obtain a fragment for integrating the first segment pyrAA-pyrAB (upstream homologous arm-$P_{trc}$-pyrAA-pyrAB-downstream homologous arm). The DNA fragment containing the target sequence was obtained by annealing primers gRNA-yjiT-S and gRNA-yjiT-A, and then ligated with the plasmid pGRB to construct a recombinant plasmid pGRB-yjiT. *E. coli* W3110 ARG7 competent cells were prepared, according to the methods described in sections 1.3 and 1.4. The plasmid pGRB-yjiT and the fragment for integrating the first segment pyrAA-pyrAB were electro-transformed into the competent cells at the same time, and finally a strain named *E. coli* W3110 ARG8 was obtained. The electropherogram of the construction of the fragment for integrating the first segment pyrAA-pyrAB and the PCR verification of the positive bacteria was shown in FIG. 9, wherein, the length of the upstream homologous arm should be 316 bp, the length of the first segment pyrAA-pyrAB gene fragment should be 2651 bp, the length of the downstream homologous arm should be 667 bp, and the full length of the integrated fragment should be 3634 bp, and the length of the fragment amplified by the identification primers should be 1100 bp, and no bands should be amplified from the original bacteria.

3.3.2 Integration of the Second Segment pyrAA-pyrAB

Figure 10:
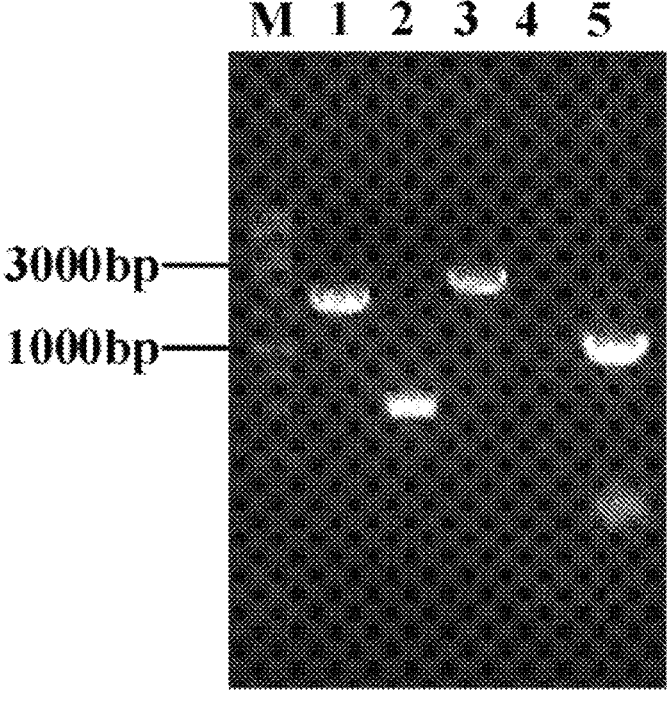
FIG. 10 shows the electropherogram of the construction and verification of the second fragment for integrating pyrAA-pyrAB, wherein M: 1 kb DNA marker; lane 1: pyrAA upstream fragment-pyrAA-pyrAB-downstream homologous arm; lane 2: downstream homologous arm; lane 3: overlapping fragment; lane 4: original strain (control); lane 5: identified fragment from positive bacteria.

Using *B. subtilis* A260 (CGMCC No. 11775) genome as the template, PCR was performed with the primers for the upstream homologous arm (2-pyrAA-pyrAB-S, 2-pyrAA-pyrAB-A) designed according to the second segment pyrAA-pyrAB and its upstream sequence to amplify the upstream downstream homologous arm (containing the 266 bp first segment pyrAA-pyrAB downstream sequence and the 1641 bp second pyrAA-pyrAB sequence, 1907 in total). Using *E. coli* W3110 (ATCC27325) genome as the template, PCR was performed with the primers for the downstream homologous arm (DN-yjiT-S1, DN-yjiT-A) designed according to the downstream sequence of its yjiT gene to amplify the downstream homologous arm of the yjiT gene. The overlap PCR method was applied to fuse the above fragments to obtain the fragment for integrating the second segment pyrAA-pyrAB (second segment pyrAA-pyrAB-downstream homologous arm). The DNA fragment containing the target sequence was obtained by annealing primers gRNA-pyrAA-pyrAB-S and gRNA-pyrAA-pyrAB-A, and then ligated with the plasmid pGRB to construct a recombinant plasmid pGRB-pyrAA-pyrAB. *E. coli* W3110 ARG8 competent cells were prepared, according to the methods described in sections 1.3 and 1.4. The plasmid pGRB-pyrAA-pyrAB and the fragment for integrating the second segment pyrAA-pyrAB were electro-transformed into the competent cells at the same time, and finally a strain named *E. coli* W3110 ARG9 was obtained. The electropherogram of the construction of the integrated fragment and the PCR verification of the positive bacteria during the second segment pyrAA-pyrAB integration process was shown in FIG. 10, wherein, the full length of the upstream sequence of the second segment pyrAA-pyrAB should be 1907 bp, the length of the downstream homologous arm should be 667 bp, and the full length of the overlapping fragment should be 2574 bp, and the length of the fragment amplified by the identification primers should be 1135 bp, and no bands should be amplified from the original bacteria.

3.4 Integration of the Lys E Gene from *Corynebacterium efficiens* into the ilvG Gene Locus in *E. coli*

Figure 11:
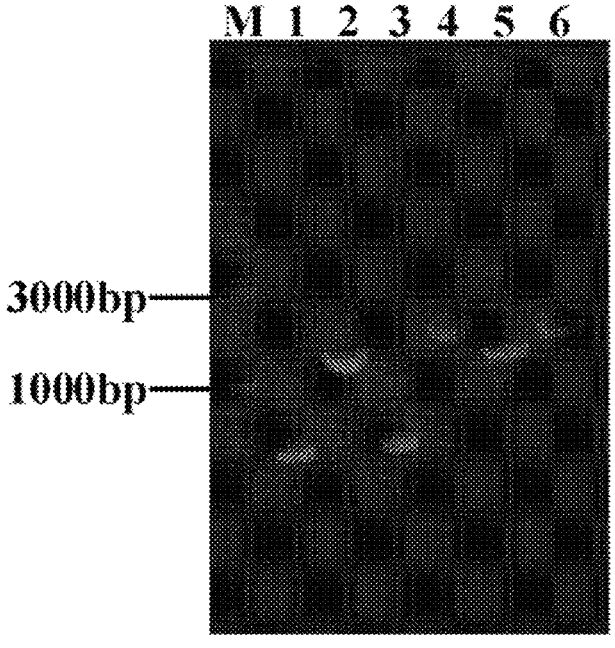
FIG. 11 shows the electropherogram of the construction and verification of the fragment for integrating lysE, wherein M: 1 kb DNA marker; lane 1: upstream homologous arm; lane 2: lysE fragment; lane 3: downstream homologous arm; lane 4: overlapping fragment; lane 5: original strain (control); lane 6: identified fragment from positive bacteria.

Using *E. coli* W3110 (ATCC27325) genome as the template, PCR was performed with the primers for the upstream homologous arm (UP-ilvG-S, UP-ilvG-A) and the primers for the downstream homologous arm (DN-ilvG-S, DN-ilvG-A) designed according to the upstream and downstream sequences of its ilvG gene to amplify the upstream and downstream homologous arms of the ilvG gene; PCR was performed with the primers (lysE-S, lysE-A) designed according to the lysE gene (NCBI Reference Sequence: WP_143758438.1) sequence (SEQ ID NO: 68) to amplify the lysE gene fragment. Promoter $P_{trc}$ was designed in the reverse primer for the upstream homologous arm and the forward primer for the lysE gene. The overlap PCR method was applied to fuse the above fragments to obtain a fragment for integrating lysE gene (upstream homologous arm-Pure-lysE-downstream homologous arm). The DNA fragment containing the target sequence was obtained by annealing primers gRNA-ilvG-S and gRNA-ilvG-A, and then ligated with the plasmid pGRB to construct a recombinant plasmid pGRB-ilvG. *E. coli* W3110 ARG9 competent cells were prepared, according to the methods described in sections 1.3 and 1.4. The plasmid pGRB-ilvG and the fragment for integrating lysE gene were electro-transformed into the competent cells at the same time, and finally a strain named *E. coli* W3110 ARG10 was obtained. The electropherogram of the construction of the integrated fragment Pirc-lysE and the PCR verification of the positive bacteria was shown in FIG. 11, wherein, the length of the upstream homologous arm should be 412 bp, the length of the Pure-lysE gene fragment should be 806 bp, the length of the downstream homologous arm should be 481 bp, and the full length of the integrated fragment should be 1699 bp, and for the PCR verification, the fragment amplified by PCR from the positive bacteria should be 1699 bp, and the fragment amplified by PCR from the original bacteria should be 1426 bp.

Example 2

The method of producing arginine by fermenting the genetically engineered strain *E. coli* W3110 ARG10 was as follows:

(1) Shake flask fermentation slant culture: inoculating the bacterial strain preserved at −80° C. onto an activated slant using the streak method, culturing at 37° C. for 12 h and passaging once;

shake flask seed culture: scraping a ring of seeds on the slant with an inoculating loop and inoculating into a 500 ml conical flask containing 30 mL of seed medium, sealing the conical flask with nine layers of gauze, and culturing at 37° C. and 200 rpm for 7-10 h;

shake flask fermentation culture: inoculating the seed culture at the concentration of 15% (v/v) into a 500 ml conical flask containing fermentation medium (final volume: 30 mL), sealing the conical flask with nine layers of gauze, culturing at 37° C. and 200 r/min in a shaking table, during the fermentation, adding ammonia water to maintain pH at 7.0-7.2; adding 60% (m/v) glucose solution to maintain fermentation; the fermentation period lasting for 26-30 h.

Components of slant medium: 1 g/L glucose, 10 g/L peptone, 10 g/L beef extract, 5 g/L yeast powder, 2.5 g/L NaCl, 20 g/L agar, the residual was water, pH 7.0-7.2.

Components of seed medium: 25 g/L glucose, 5 g/L yeast extract, 3 g/L peptone, 1 g/L $K_2HPO_4$, 1 g/L $MgSO_4.7H_2O$, 10 mg/L $FeSO_4.7H_2O$, 10 mg/L $MnSO_4.7H_2O$, 1 mg/L each of $V_{B1}$, $V_{B3}$, $V_{B5}$, $V_{B12}$ and $V_H$, the residual was water, pH 7.0-7.2.

Components of fermentation medium: 25 g/L glucose, 3 g/L yeast extract, 2 g/L peptone, 3 g/L $K_2HPO_4$, 2 g/L $MgSO_4.7H_2O$, 10 mg/L $FeSO_4.7H_2O$, 10 mg/L $MnSO_4.7H_2O$, 1 mg/L each of $V_{B1}$, $V_{B3}$, $V_{B5}$, $V_{B12}$ and $V_H$, the residual was water, pH 7.0-7.2.

After 26-30 h shake flask fermentation, the yield of L-arginine in the fermentation broth of *E. coli* W3110 ARG10 strain was 30-32 g/L.

(2) Fermenter fermentation slant activation culture: scraping a ring of the bacterial strain preserved at −80° C. and spreading evenly onto an activated slant, culturing at 37° C. for 12-16 h and transferring to an eggplant-shaped flask to continue the culture for 12-16 h;

seed culture: taking an appropriate amount of sterilized water into the eggplant-shaped flask, inoculating the bacterial suspension into the seed medium, keeping pH at about 7.0, the temperature at 37° C. and the dissolved oxygen between 25-35%, and culturing the cells until reaching 5-6 g/L dry weight of cells;

fermentation culture: inoculating the seed culture at the concentration of 15% into a fresh fermentation medium, starting fermentation and during the fermentation process, keeping pH stable at about 7.0, temperature at 35° C. and dissolved oxygen between 25-35%; when the glucose in the medium was exhausted, 80% (m/v) glucose solution was added to maintain the glucose concentration in the fermentation medium at 0.1-5 g/L.

The slant medium, seed medium and fermentation medium were the same as that in the shake flask fermentation . . .

Figure 12:
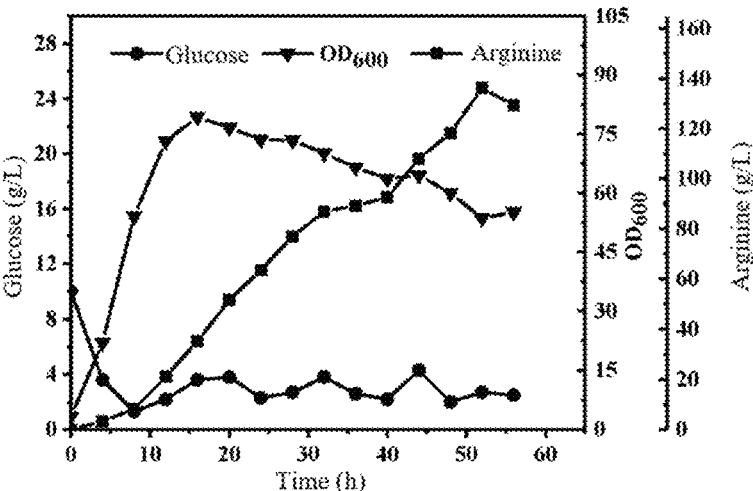
FIG. 12 shows the fed-batch fermentation curve of the strain E. coli W3110 ARG10 in a 5 L fermenter.

The accumulation of L-arginine reached 130-135 g/L after culture for 50-55 h in a 5 L fermenter. The conversion rate was 0.48 g arginine/g glucose, and the production intensity was 2.5 g arginine/L/h. The fermentation curve is shown in FIG. 12.

The embodiments of the present invention are described above. However, the present invention is not limited to the above embodiments. Any modification, equivalent replacement, improvement, etc. made within the spirit and principles of the present invention shall be included in the protection scope of the invention.

The invention claimed is:

1. A construction method of a genetically engineered bacterial strain, comprising the following steps:

(1) integrating pyrAA and pyrAB genes into a genome of *Escherichia coli* used as a starting strain;

(2) integrating at least one arginine biosynthesis pathway enzyme gene selected from the group consisting of argC, argJ, argB, argD, argF, argG, and argH genes; and integrating lysE gene encoding an arginine transporter; and (3) knocking out a gene encoding an arginine decarboxylase, a gene encoding an arginine succinyltransferase, and a gene encoding an acetylornithine deacetylase;

wherein, the gene encoding an acetylornithine deacetylase includes at least one of speA and adiA genes;

the gene encoding an arginine succinyltransferase is astA gene; and the gene encoding an acetylornithine deacetylase is the argE gene.

2. The construction method according to claim 1, wherein the construction method comprises the steps of:

(1) knocking out the following three genes in *E. coli*: speA gene encoding an arginine decarboxylase, adiA gene encoding an arginine decarboxylase and astA gene encoding an arginine succinyltransferase;

(2) knocking out argE gene encoding an acetylornithine deacetylase in *E. coli*, and optionally integrating gene argJ encoding a glutamate acetyltransferase into *E. coli*;

(3) integrating the following arginine biosynthesis-related gene cluster: argC, argJ, argB, argD, argF, argG and argH;

(4) integrating pyrAA and pyrAB genes encoding a carbamoyl phosphate synthetase; and (5) integrating lysE gene encoding an arginine transporter into the *E. coli* genome.

3. The construction method according to claim 1, comprising adopting CRISPR/Cas9-mediated gene editing technology to perform gene integration and knockout.

4. The construction method according to claim 1, comprising the steps of simultaneously transforming a pGRB plasmid and a recombinant fragment into electroporation-competent cells containing pREDCas9 and eliminating plasmids, to obtain a recombinant genetically engineered bacterial strain;

the step of constructing the pGRB plasmid comprises: designing a target sequence, preparing a DNA fragment comprising the target sequence, and recombining the DNA fragment comprising the target sequence with a linearized vector fragment;

in the construction method, the step of constructing a recombinant fragment comprises constructing a recombinant fragment for gene integration or for gene knockout;

the step of constructing a recombinant fragment for gene integration comprises: using the genome of the starting strain as a template, designing primers for the upstream and downstream homologous arms according to the upstream and downstream sequences of the intended insertion site of the target gene, and designing primers according to the target genome to amplify the target gene fragment, and then performing overlap PCR to obtain the recombinant fragment; and the step of constructing a recombinant fragment for gene knockout comprises: using the upstream and downstream sequences of the gene to be knocked out as templates, designing primers for upstream and downstream homologous arms; respectively amplifying the upstream and downstream homologous arms by PCR, and then preparing the recombinant fragment by overlap PCR.

5. The construction method according to claim 1, wherein the pyrAA and pyrAB genes are derived from the genes encoding a carbamoyl phosphate synthetase in *B. subtilis* A260.

6. The construction method according to claim 1, wherein the *Escherichia coli* is *E. coli* W3110.

* * * * *